United States Patent [19]
Keränen et al.

[11] Patent Number: 5,789,193
[45] Date of Patent: Aug. 4, 1998

[54] INCREASED PRODUCTION OF SECRETED PROTEINS BY RECOMBINANT EUKARYOTIC CELLS

[75] Inventors: Sirkka Keränen; Markku Aalto; Mika Outola, all of Helsinki; Hans Ronne, Upsala; Merja Penttilä, Helsinki, all of Finland

[73] Assignee: Valtion Teknillinen Tutkimuskeskus, Espoo, Finland

[21] Appl. No.: 411,706

[22] PCT Filed: Oct. 6, 1993

[86] PCT No.: PCT/FI93/00402

§ 371 Date: Jan. 16, 1996

§ 102(e) Date: Jan. 16, 1996

[87] PCT Pub. No.: WO94/08024

PCT Pub. Date: Apr. 14, 1994

[30] Foreign Application Priority Data

Oct. 6, 1992 [FI] Finland .................................. 924494

[51] Int. Cl.$^6$ .................................................. C12P 21/06
[52] U.S. Cl. ...................... 435/69.1; 435/71.1; 435/171; 435/172.3; 435/254.2; 435/254.21; 435/254.6; 435/255.6; 435/254.3; 435/256.7; 536/23.1
[58] Field of Search .................... 536/23.1; 435/69.1, 435/320.1, 254.11, 71.1, 171, 172.3, 255.2, 255.5, 255.6, 256.1, 256.7, 254.2, 254.21, 254.6, 254.3

[56] References Cited

FOREIGN PATENT DOCUMENTS 0 284 044   9/1988   European Pat. Off. .

OTHER PUBLICATIONS

Mohamed, A.H., et al. 1988. Journal of Biological Chemistry. vol. 263. No. 25, pp. 12315–12325. "Primary Structure of the Multisubunit . . .".

Mohamed, A. H., et al. 1989. Gen Bank Accession No. J03936.

Bennett, M.K, et al. Science vol. 257, 10 Jul. 1992. pp. 255–259. "Syntaxin: A Synaptic Protein Implizated in Docking . . .".

Inoue, et al., "Cloning and Sequence Analysis of cDNA for a Neuronal Cell Membrane Antigen, HPC–1", *The Journal of Biological Chemistry* 267(15):10613–10619, (May 1992).

Martegani, et al., "Expression of high levels of human tissue plasminogen activator in yeast under the control of an inducible GAL promoter", *Applied Microbiology and Biotechnology* 37:604–608, (1992).

Hirai, et al., "Epimorphin: A Mesenchymal Protein Essential for Epithelial Morphogenesis", *Cell* 69:471–481 (May 1, 1992).

Aalto et al., "Yeast syntaxins Sso1p and Sso2p belong to a family of related membrane proteins that function in vesicular transport," *EMBO J.*, 12(11):4095–4104(1993).

Bennett et al., "The molecular machinery for secretion is conserved from yeast to neurons, " *Proc. Nat'l Acad. Sci., USA*, 90:2559–2563 (1993).

Case et al., "Efficient transformation of *Neurospora crassa* by utilizing hybrid plasmid DNA," *Proc. Nat'l Acad. Sci., USA*, 76(10):5259–5263 (Oct., 1979).

Ferro–Novick et al., Vesicle fusion from yeast to man, *Nature*, 370:191–193 (Jul. 21, 1994).

Jeenes et al., "Heterologous Protein Production by Filamentous Fungi," *Biotechnology and Genetic Reviews*, 9:327–367 (Dec., 1991).

Penttilä et al., "A versatile transformation system for the cellulolytic filamentous fungus *Trichoderma reesei*," *Gene*, 61:155–164 (1987).

Südhof et al., "Membrane Fusion Machinery: Insights from Synaptic Proteins," *Cell*, 75:1–4 (Oct. 8, 1993).

Tilburn et al., "Transformation by integration in *Aspergillus nidulans*," *Gene*, 26:205–221 (1983).

Primary Examiner—James Ketter
Assistant Examiner—Irem Yucel
Attorney, Agent, or Firm—Marshall, O'Toole, Gerstein, Murray & Borun

[57] ABSTRACT

The invention relates to recombinant DNA technology. Specifically this invention relates to new recombinant eukaryotic cells transformed with SSO genes. Eukaryotic cells transformed with several copies of SSO genes, or overexpressing the Sso protein by some other means, have an increased capacity to produce secreted foreign or endogenous proteins. Further, the said new recombinant cells, when transformed with genes expressing suitable hydrolytic enzymes can utilize appropriate macromolecular compounds more efficiently, which results in increased cell mass production and/or more versatile utilization of the compounds in relevant biotechnical applications.

23 Claims, 8 Drawing Sheets

1. *Saccharomyces cerevisiae*
2. *Schizosaccharomyces pombe*
3. *Kluyveromyces lactis*
4. *Pichia stipitis*
5. *Aspergillus nidulans*
6. *Trichoderma reesei*
7. plasmid control

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 870 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Saccharomyces cerevisiae
        ( B ) STRAIN: X 2180-1B ( i x ) FEATURE:
        ( A ) NAME/KEY: CDS
        ( B ) LOCATION: 1..870

( x i ) SEQUENCE DESCRIPTION: SEQ ID NO: 1:

```
ATG AGT TAT AAT AAT CCG TAC CAG TTG GAA ACC CCT TTT GAA GAG TCA        48
Met Ser Tyr Asn Asn Pro Tyr Gln Leu Glu Thr Pro Phe Glu Glu Ser
 1               5                  10                  15

TAC GAG TTG GAC GAA GGT TCG AGC GCT ATC GGT GCT GAA GGC CAC GAT        96
Tyr Glu Leu Asp Glu Gly Ser Ser Ala Ile Gly Ala Glu Gly His Asp
            20                  25                  30

TTC GTG GGC TTC ATG AAT AAG ATC AGT CAA ATC AAT CGC GAT CTC GAT       144
Phe Val Gly Phe Met Asn Lys Ile Ser Gln Ile Asn Arg Asp Leu Asp
        35                  40                  45

AAG TAC GAC CAT ACC ATC AAC CAG GTC GAT TCT TTG CAT AAG AGG CTA       192
Lys Tyr Asp His Thr Ile Asn Gln Val Asp Ser Leu His Lys Arg Leu
    50                  55                  60

CTG ACC GAA GTT AAT GAG GAG CAA GCA AGT CAC TTA AGG CAC TCC CTG       240
Leu Thr Glu Val Asn Glu Glu Gln Ala Ser His Leu Arg His Ser Leu
65                  70                  75                  80

GAC AAC TTC GTC GCA CAA GCC ACG GAC TTG CAG TTC AAA CTG AAA AAT       288
Asp Asn Phe Val Ala Gln Ala Thr Asp Leu Gln Phe Lys Leu Lys Asn
                85                  90                  95

GAG ATT AAA AGT GCC CAA AGG GAT GGG ATA CAT GAC ACC AAC AAG CAA       336
Glu Ile Lys Ser Ala Gln Arg Asp Gly Ile His Asp Thr Asn Lys Gln
            100                 105                 110

GCT CAG GCG GAA AAC TCC AGA CAA AGA TTT TTG AAG CTT ATC CAG GAC       384
Ala Gln Ala Glu Asn Ser Arg Gln Arg Phe Leu Lys Leu Ile Gln Asp
        115                 120                 125

TAC AGA ATT GTG GAT TCC AAC TAC AAG GAG GAG AAT AAA GAG CAA GCC       432
Tyr Arg Ile Val Asp Ser Asn Tyr Lys Glu Glu Asn Lys Glu Gln Ala
    130                 135                 140

AAG AGG CAG TAT ATG ATC ATT CAA CCA GAG GCC ACC GAA GAT GAA GTT       480
Lys Arg Gln Tyr Met Ile Ile Gln Pro Glu Ala Thr Glu Asp Glu Val
145                 150                 155                 160
```

| | | | | | | | | | | | | | | | | |
|---|---|---|---|---|---|---|---|---|---|---|---|---|---|---|---|---|
| GAA | GCA | GCC | ATA | AGC | GAT | GTA | GGG | GGC | CAG | CAG | ATC | TTC | TCA | CAA | GCA | 528 |
| Glu | Ala | Ala | Ile | Ser | Asp | Val | Gly | Gly | Gln | Gln | Ile | Phe | Ser | Gln | Ala | |
| | | | | 165 | | | | | 170 | | | | | 175 | | |
| TTG | TTG | AAT | GCT | AAC | AGA | CGT | GGG | GAA | GCC | AAG | ACT | GCT | CTT | GCG | GAA | 576 |
| Leu | Leu | Asn | Ala | Asn | Arg | Arg | Gly | Glu | Ala | Lys | Thr | Ala | Leu | Ala | Glu | |
| | | | | 180 | | | | | 185 | | | | | 190 | | |
| GTC | CAG | GCA | AGG | CAC | CAA | GAG | TTA | TTG | AAA | CTA | GAA | AAA | TCC | ATG | GCA | 624 |
| Val | Gln | Ala | Arg | His | Gln | Glu | Leu | Leu | Lys | Leu | Glu | Lys | Ser | Met | Ala | |
| | | | 195 | | | | | 200 | | | | | 205 | | | |
| GAA | CTT | ACT | CAA | TTG | TTT | AAT | GAC | ATG | GAA | GAA | CTG | GTA | ATA | GAA | CAA | 672 |
| Glu | Leu | Thr | Gln | Leu | Phe | Asn | Asp | Met | Glu | Glu | Leu | Val | Ile | Glu | Gln | |
| | | 210 | | | | | 215 | | | | | 220 | | | | |
| CAA | GAA | AAC | GTA | GAC | GTC | ATC | GAC | AAG | AAC | GTT | GAA | GAC | GCT | CAA | CTC | 720 |
| Gln | Glu | Asn | Val | Asp | Val | Ile | Asp | Lys | Asn | Val | Glu | Asp | Ala | Gln | Leu | |
| 225 | | | | | 230 | | | | | 235 | | | | | 240 | |
| GAC | GTA | GAA | CAG | GGT | GTC | GGT | CAT | ACC | GAT | AAA | GCC | GTC | AAG | AGT | GCC | 768 |
| Asp | Val | Glu | Gln | Gly | Val | Gly | His | Thr | Asp | Lys | Ala | Val | Lys | Ser | Ala | |
| | | | | 245 | | | | | 250 | | | | | 255 | | |
| AGA | AAA | GCA | AGA | AAG | AAC | AAG | ATT | AGA | TGT | TGG | TTG | ATT | GTA | TTC | GCC | 816 |
| Arg | Lys | Ala | Arg | Lys | Asn | Lys | Ile | Arg | Cys | Trp | Leu | Ile | Val | Phe | Ala | |
| | | | 260 | | | | | 265 | | | | | 270 | | | |
| ATC | ATT | GTA | GTC | GTT | GTT | GTC | GTT | GTT | GTC | CCA | GCC | GTT | GTC | AAA | | 864 |
| Ile | Ile | Val | Val | Val | Val | Val | Val | Val | Val | Pro | Ala | Val | Val | Lys | | |
| | | 275 | | | | | 280 | | | | | 285 | | | | |
| ACG | CGT | | | | | | | | | | | | | | | 870 |
| Thr | Arg | | | | | | | | | | | | | | | |
| 290 | | | | | | | | | | | | | | | | |

( 2 ) INFORMATION FOR SEQ ID NO: 2:

( i ) SEQUENCE CHARACTERISTICS:
        ( A ) LENGTH: 290 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Met | Ser | Tyr | Asn | Asn | Pro | Tyr | Gln | Leu | Glu | Thr | Pro | Phe | Glu | Glu | Ser |
| 1 | | | | 5 | | | | | 10 | | | | | 15 | |
| Tyr | Glu | Leu | Asp | Glu | Gly | Ser | Ser | Ala | Ile | Gly | Ala | Glu | Gly | His | Asp |
| | | | 20 | | | | | 25 | | | | | 30 | | |
| Phe | Val | Gly | Phe | Met | Asn | Lys | Ile | Ser | Gln | Ile | Asn | Arg | Asp | Leu | Asp |
| | | 35 | | | | | 40 | | | | | 45 | | | |
| Lys | Tyr | Asp | His | Thr | Ile | Asn | Gln | Val | Asp | Ser | Leu | His | Lys | Arg | Leu |
| | 50 | | | | | 55 | | | | | 60 | | | | |
| Leu | Thr | Glu | Val | Asn | Glu | Glu | Gln | Ala | Ser | His | Leu | Arg | His | Ser | Leu |
| 65 | | | | | 70 | | | | | 75 | | | | | 80 |
| Asp | Asn | Phe | Val | Ala | Gln | Ala | Thr | Asp | Leu | Gln | Phe | Lys | Leu | Lys | Asn |
| | | | | 85 | | | | | 90 | | | | | 95 | |
| Glu | Ile | Lys | Ser | Ala | Gln | Arg | Asp | Gly | Ile | His | Asp | Thr | Asn | Lys | Gln |
| | | | 100 | | | | | 105 | | | | | 110 | | |
| Ala | Gln | Ala | Glu | Asn | Ser | Arg | Gln | Arg | Phe | Leu | Lys | Leu | Ile | Gln | Asp |
| | | 115 | | | | | 120 | | | | | 125 | | | |
| Tyr | Arg | Ile | Val | Asp | Ser | Asn | Tyr | Lys | Glu | Glu | Asn | Lys | Glu | Gln | Ala |
| | 130 | | | | | 135 | | | | | 140 | | | | |
| Lys | Arg | Gln | Tyr | Met | Ile | Ile | Gln | Pro | Glu | Ala | Thr | Glu | Asp | Glu | Val |
| 145 | | | | | 150 | | | | | 155 | | | | | 160 |
| Glu | Ala | Ala | Ile | Ser | Asp | Val | Gly | Gly | Gln | Gln | Ile | Phe | Ser | Gln | Ala |
| | | | | 165 | | | | | 170 | | | | | 175 | |

```
Leu  Leu  Asn  Ala  Asn  Arg  Arg  Gly  Glu  Ala  Lys  Thr  Ala  Leu  Ala  Glu
               180                     185                    190

Val  Gln  Ala  Arg  His  Gln  Glu  Leu  Leu  Lys  Leu  Glu  Lys  Ser  Met  Ala
          195                    200                    205

Glu  Leu  Thr  Gln  Leu  Phe  Asn  Asp  Met  Glu  Glu  Leu  Val  Ile  Glu  Gln
     210                         215                    220

Gln  Glu  Asn  Val  Asp  Val  Ile  Asp  Lys  Asn  Val  Glu  Asp  Ala  Gln  Leu
225                      230                    235                         240

Asp  Val  Glu  Gln  Gly  Val  Gly  His  Thr  Asp  Lys  Ala  Val  Lys  Ser  Ala
                    245                     250                    255

Arg  Lys  Ala  Arg  Lys  Asn  Lys  Ile  Arg  Cys  Trp  Leu  Ile  Val  Phe  Ala
               260                     265                    270

Ile  Ile  Val  Val  Val  Val  Val  Val  Val  Val  Val  Pro  Ala  Val  Val  Lys
               275                     280                    285

Thr  Arg
290
```

( 2 ) INFORMATION FOR SEQ ID NO: 3:

( i ) SEQUENCE CHARACTERISTICS:
        ( A ) LENGTH: 885 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Saccharomyces cerevisiae
        ( B ) STRAIN: X 2180-1B ( i x ) FEATURE:
        ( A ) NAME/KEY: CDS
        ( B ) LOCATION: 1..885

( x i ) SEQUENCE DESCRIPTION: SEQ ID NO: 3:

```
ATG  AGC  AAC  GCT  AAT  CCT  TAT  GAG  AAT  AAC  AAT  CCG  TAC  GCT  GAA  AAC       48
Met  Ser  Asn  Ala  Asn  Pro  Tyr  Glu  Asn  Asn  Asn  Pro  Tyr  Ala  Glu  Asn
1                   5                        10                      15

TAT  GAA  ATG  CAA  GAG  GAC  TTG  AAC  AAT  GCT  CCT  ACT  GGT  CAC  TCA  GAT       96
Tyr  Glu  Met  Gln  Glu  Asp  Leu  Asn  Asn  Ala  Pro  Thr  Gly  His  Ser  Asp
               20                       25                      30

GGT  AGC  GAC  GAT  TTC  GTA  GCT  TTT  ATG  AAC  AAG  ATC  AAC  TCA  ATA  AAT      144
Gly  Ser  Asp  Asp  Phe  Val  Ala  Phe  Met  Asn  Lys  Ile  Asn  Ser  Ile  Asn
          35                       40                      45

GCT  AAC  TTG  TCC  AGG  TAC  GAA  AAC  ATT  ATC  AAC  CAA  ATT  GAT  GCG  CAA      192
Ala  Asn  Leu  Ser  Arg  Tyr  Glu  Asn  Ile  Ile  Asn  Gln  Ile  Asp  Ala  Gln
     50                       55                      60

CAC  AAA  GAC  CTA  CTT  ACT  CAA  GTG  AGT  GAG  GAA  CAG  GAG  ATG  GAA  TTG      240
His  Lys  Asp  Leu  Leu  Thr  Gln  Val  Ser  Glu  Glu  Gln  Glu  Met  Glu  Leu
65                  70                       75                           80

AGA  CGT  TCT  TTG  GAC  GAT  TAC  ATC  TCT  CAG  GCC  ACA  GAT  TTG  CAG  TAT      288
Arg  Arg  Ser  Leu  Asp  Asp  Tyr  Ile  Ser  Gln  Ala  Thr  Asp  Leu  Gln  Tyr
                    85                       90                          95

CAA  TTG  AAA  GCG  GAT  ATC  AAA  GAT  GCC  CAG  AGA  GAC  GGA  TTG  CAC  GAC      336
Gln  Leu  Lys  Ala  Asp  Ile  Lys  Asp  Ala  Gln  Arg  Asp  Gly  Leu  His  Asp
               100                      105                     110

TCT  AAT  AAA  CAG  GCA  CAA  GCT  GAA  AAT  TGC  AGA  CAG  AAA  TTC  TTA  AAA      384
Ser  Asn  Lys  Gln  Ala  Gln  Ala  Glu  Asn  Cys  Arg  Gln  Lys  Phe  Leu  Lys
          115                      120                     125

TTA  ATT  CAA  GAC  TAC  AGA  ATT  ATC  GAT  TCT  AAC  TAC  AAA  GAA  GAA  AGC      432
Leu  Ile  Gln  Asp  Tyr  Arg  Ile  Ile  Asp  Ser  Asn  Tyr  Lys  Glu  Glu  Ser
```

|     |     |     |     | 130 |     |     |     |     | 135 |     |     |     |     | 140 |     |     |
|-----|-----|-----|-----|-----|-----|-----|-----|-----|-----|-----|-----|-----|-----|-----|-----|-----|
| AAA | GAG | CAG | GCG | AAG | AGA | CAG | TAC | ACA | ATT | ATC | CAA | CCG | GAA | GCC | ACT | 480 |
| Lys | Glu | Gln | Ala | Lys | Arg | Gln | Tyr | Thr | Ile | Ile | Gln | Pro | Glu | Ala | Thr |     |
| 145 |     |     |     | 150 |     |     |     |     | 155 |     |     |     |     | 160 |     |     |
| GAC | GAA | GAA | GTG | GAA | GCC | GCC | ATC | AAC | GAT | GTC | AAT | GGC | CAG | CAG | ATC | 528 |
| Asp | Glu | Glu | Val | Glu | Ala | Ala | Ile | Asn | Asp | Val | Asn | Gly | Gln | Gln | Ile |     |
|     |     |     |     | 165 |     |     |     |     | 170 |     |     |     |     | 175 |     |     |
| TTT | TCC | CAA | GCG | TTG | CTA | AAC | GCC | AAT | AGA | CGT | GGT | GAG | GCC | AAG | ACA | 576 |
| Phe | Ser | Gln | Ala | Leu | Leu | Asn | Ala | Asn | Arg | Arg | Gly | Glu | Ala | Lys | Thr |     |
|     |     |     |     | 180 |     |     |     |     | 185 |     |     |     |     | 190 |     |     |
| GCA | TTG | GCC | GAA | GTA | CAG | GCT | AGA | CAT | CAA | GAG | TTG | TTG | AAG | TTG | GAA | 624 |
| Ala | Leu | Ala | Glu | Val | Gln | Ala | Arg | His | Gln | Glu | Leu | Leu | Lys | Leu | Glu |     |
|     |     |     |     | 195 |     |     |     |     | 200 |     |     |     |     | 205 |     |     |
| AAA | ACA | ATG | GCT | GAA | CTT | ACC | CAA | TTG | TTC | AAT | GAC | ATG | AAA | GAG | TTG | 672 |
| Lys | Thr | Met | Ala | Glu | Leu | Thr | Gln | Leu | Phe | Asn | Asp | Met | Lys | Glu | Leu |     |
|     |     |     |     | 210 |     |     |     |     | 215 |     |     |     |     | 220 |     |     |
| GTC | ATC | GAA | CAA | CAA | GAA | AAT | GTG | GAT | GTC | ATT | GAC | AAA | AAC | GTC | GAA | 720 |
| Val | Ile | Glu | Gln | Gln | Glu | Asn | Val | Asp | Val | Ile | Asp | Lys | Asn | Val | Glu |     |
| 225 |     |     |     |     | 230 |     |     |     |     | 235 |     |     |     |     | 240 |     |
| GAC | GCT | CAG | CAA | GAT | GTA | GAG | CAA | GGT | GTG | GGT | CAC | ACC | AAC | AAG | GCC | 768 |
| Asp | Ala | Gln | Gln | Asp | Val | Glu | Gln | Gly | Val | Gly | His | Thr | Asn | Lys | Ala |     |
|     |     |     |     | 245 |     |     |     |     | 250 |     |     |     |     | 255 |     |     |
| GTT | AAG | AGT | GCC | AGA | AAA | GCA | AGA | AAA | AAC | AAA | ATA | AGA | TGT | TTG | ATC | 816 |
| Val | Lys | Ser | Ala | Arg | Lys | Ala | Arg | Lys | Asn | Lys | Ile | Arg | Cys | Leu | Ile |     |
|     |     |     |     | 260 |     |     |     |     | 265 |     |     |     |     | 270 |     |     |
| ATC | TGC | TTT | ATT | ATC | TTT | GCT | ATT | GTT | GTT | GTC | GTT | GTG | GTT | GTT | CCA | 864 |
| Ile | Cys | Phe | Ile | Ile | Phe | Ala | Ile | Val | Val | Val | Val | Val | Val | Val | Pro |     |
|     |     |     |     | 275 |     |     |     |     | 280 |     |     |     |     | 285 |     |     |
| TCC | GTT | GTG | GAA | ACA | AGA | AAG |     |     |     |     |     |     |     |     |     | 885 |
| Ser | Val | Val | Glu | Thr | Arg | Lys |     |     |     |     |     |     |     |     |     |     |
|     |     |     |     | 290 |     | 295 |     |     |     |     |     |     |     |     |     |     |

( 2 ) INFORMATION FOR SEQ ID NO: 4:

( i ) SEQUENCE CHARACTERISTICS:
        ( A ) LENGTH: 295 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

| Met | Ser | Asn | Ala | Asn | Pro | Tyr | Glu | Asn | Asn | Pro | Tyr | Ala | Glu | Asn |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Tyr | Glu | Met | Gln | Glu | Asp | Leu | Asn | Asn | Ala | Pro | Thr | Gly | His | Ser | Asp |
|     |     |     | 20  |     |     |     |     | 25  |     |     |     |     | 30  |     |     |
| Gly | Ser | Asp | Asp | Phe | Val | Ala | Phe | Met | Asn | Lys | Ile | Asn | Ser | Ile | Asn |
|     |     |     | 35  |     |     |     |     | 40  |     |     |     |     | 45  |     |     |
| Ala | Asn | Leu | Ser | Arg | Tyr | Glu | Asn | Ile | Ile | Asn | Gln | Ile | Asp | Ala | Gln |
|     |     | 50  |     |     |     |     | 55  |     |     |     |     | 60  |     |     |     |
| His | Lys | Asp | Leu | Leu | Thr | Gln | Val | Ser | Glu | Glu | Gln | Glu | Met | Glu | Leu |
| 65  |     |     |     |     | 70  |     |     |     |     | 75  |     |     |     |     | 80  |
| Arg | Arg | Ser | Leu | Asp | Asp | Tyr | Ile | Ser | Gln | Ala | Thr | Asp | Leu | Gln | Tyr |
|     |     |     |     | 85  |     |     |     |     | 90  |     |     |     |     | 95  |     |
| Gln | Leu | Lys | Ala | Asp | Ile | Lys | Asp | Ala | Gln | Arg | Asp | Gly | Leu | His | Asp |
|     |     |     | 100 |     |     |     |     | 105 |     |     |     |     | 110 |     |     |
| Ser | Asn | Lys | Gln | Ala | Gln | Ala | Glu | Asn | Cys | Arg | Gln | Lys | Phe | Leu | Lys |
|     |     | 115 |     |     |     |     | 120 |     |     |     |     | 125 |     |     |     |
| Leu | Ile | Gln | Asp | Tyr | Arg | Ile | Ile | Asp | Ser | Asn | Tyr | Lys | Glu | Glu | Ser |
| 130 |     |     |     |     | 135 |     |     |     |     | 140 |     |     |     |     |     |

| Lys 145 | Glu | Gln | Ala | Lys | Arg 150 | Gln | Tyr | Thr | Ile | Ile 155 | Gln | Pro | Glu | Ala | Thr 160 |
|---|---|---|---|---|---|---|---|---|---|---|---|---|---|---|---|
| Asp | Glu | Glu | Val | Glu 165 | Ala | Ala | Ile | Asn | Asp 170 | Val | Asn | Gly | Gln | Gln 175 | Ile |
| Phe | Ser | Gln | Ala 180 | Leu | Leu | Asn | Ala | Asn 185 | Arg | Arg | Gly | Glu | Ala 190 | Lys | Thr |
| Ala | Leu | Ala 195 | Glu | Val | Gln | Ala | Arg 200 | His | Gln | Glu | Leu | Leu 205 | Lys | Leu | Glu |
| Lys | Thr 210 | Met | Ala | Glu | Leu | Thr 215 | Gln | Leu | Phe | Asn | Asp 220 | Met | Lys | Glu | Leu |
| Val 225 | Ile | Glu | Gln | Gln | Glu 230 | Asn | Val | Asp | Val | Ile 235 | Asp | Lys | Asn | Val | Glu 240 |
| Asp | Ala | Gln | Gln | Asp 245 | Val | Glu | Gln | Gly | Val 250 | Gly | His | Thr | Asn | Lys 255 | Ala |
| Val | Lys | Ser | Ala 260 | Arg | Lys | Ala | Arg | Lys 265 | Asn | Lys | Ile | Arg | Cys 270 | Leu | Ile |
| Ile | Cys | Phe 275 | Ile | Ile | Phe | Ala | Ile 280 | Val | Val | Val | Val | Val 285 | Val | Val | Pro |
| Ser | Val 290 | Val | Glu | Thr | Arg | Lys 295 | | | | | | | | | |

1

INCREASED PRODUCTION OF SECRETED PROTEINS BY RECOMBINANT EUKARYOTIC CELLS

FIELD OF THE INVENTION

This invention relates to recombinant-DNA-technology. Specifically this invention relates to new recombinant eukaryotic cells transformed with SSO genes or their homologues. A eukaryotic cell transformed with several copies of a SSO gene or a gene homologous to SSO has an increased capacity to produce secreted foreign or endogenous proteins.

Further, the said new recombinant eukaryotic cells, especially yeasts and filamentous fungi, when transformed with genes expressing suitable hydrolytic enzymes can hydrolyze and/or utilize appropriate macromolecular/polymeric compounds more efficiently, which results in increased cell mass production and/or more versatile utilization of the compounds in relevant biotechnical applications.

BACKGROUND OF THE INVENTION

The development of recombinant DNA methods has made it possible to produce proteins in heterologous host systems. This possibility greatly facilitates production of e.g. proteins of therapeutic importance which normally occur in nature in very low amounts or are otherwise difficult to isolate or purify. Such proteins include growth factors, hormones and other biologically active proteins or peptides which traditionally have been isolated from human or animal tissues or body fluids e.g. blood serum or urine. The increasing danger of the presence of human pathogenic viruses such as HBV, HIV, and oncogenic viruses or other pathogens in the human or animal tissues or body fluids has greatly speeded up the search for heterologous production systems for these therapeutics. Other proteins of clinical importance are viral or other microbial or human parasite proteins needed for diagnostics and for vaccines especially of such organisms which are difficult to grow in vitro or in tissue culture, or are dangerous human pathogens. These include viruses like HBV, HIV, yellow fever, rubella, FMDV, rabies, and human parasites such as malaria.

A further group of proteins for which heterologous production systems have been or are being developed are secreted enzymes, especially those hydrolyzing plant material, and which are needed in food and fodder production as well as in other industrial processes including textile industry and pulp and paper industry. The possibility of producing proteins in heterologous systems or production of endogenous proteins in genetically engineered cells increases their yields and greatly facilitates their purification and has already by now had a great impact on studies of structure and function of many important enzymes and other proteins. The production and secretion of foreign hydrolytic enzymes in yeast for example, results in improvements in processes based on industrial yeast strains such as distiller's, brewer's or baker's yeasts.

Various production systems have been and are being developed including bacteria, yeasts, filamentous fungi, animal and plant cell cultures and even multicellular organisms like transgenic animals and plants. All of these different systems have their advantages, even if disadvantages, and all of them are needed.

The yeast *Saccharomyces cerevisiae* is at the moment the best known eukaryote at genetic level. As a eukaryotic microbe it possesses the advantages of a eukaryotic cell like most if not all of the post-translational modifications of eukaryotes, and as a microbe it shares the easy handling and cultivation properties of bacteria. The large scale fermentation systems are well developed for *S. cerevisiae* which has a long history as a work horse of biotechnology including production of food ingredients and beverages such as beer and wine.

The yeast genetic methods are by far the best developed among eukaryotes based on the vast knowledge obtained by classical genetics. This made it easy to adopt and further develop for yeast the gene technology procedures first described for *Escherichia coli*. Along other lines the methods for constructing yeast strains producing foreign proteins have been developed to a great extent (Romanos et. al., 1992).

Secretion of the proteins into the culture medium involves transfer of the proteins through the various membrane enclosed compartments constituting the secretory pathway. First the proteins are translocated into the lumen of the endoplasmic reticulum ER. From there on the proteins are transported in membrane vesicles to the Golgi complex and from Golgi to plasma membrane. The secretory process involves several steps in which vesicles containing the secreted proteins are pinched off from the donor membrane, targetted to and fused with the acceptor membrane. At each of these steps function of several different proteins are needed.

The yeast secretory pathway and a great number of genes involved in it have been elucidated by isolation of conditional lethal mutants deficient in certain steps of the secretory process (Novick et al., 1980; 1981). Mutation in a protein, needed for a particular transfer step results in accumulation of the secreted proteins in the preceding membrane compartment. Thus proteins can accumulate at ER, Golgi or in vesicles between ER and Golgi, or in vesicles between Golgi and plasma membrane.

More detailed analysis of the genes and proteins involved in the secretory process has become possible upon cloning the genes and characterization of the function of the corresponding proteins. A picture is emerging which indicates that in all steps several interacting proteins are functioning. We have recently cloned two new yeast genes, SSO1 and SSO2 as multicopy suppressors of sec1-1 defect in growth and secretion in elevated temperatures (Aalto et al., 1993).

Many of the genes identified in and isolated from *S. cerevisiae* have been found and cloned from other organisms based either on the sequence homology with yeast genes or complementation of yeast mutations. Mammalian NSF factor is the homologue of yeast SEC18 gene product and displays a similar function in protein secretion (Wilson et al., 1989). SEC14 gene of *Yarrowia lipolytica* (Lopez et al., 1992) has been cloned and characterized. Mammalian homologue for yeast SEC11 gene coding for a component of the signal peptidase has been cloned (Greenberg et al., 1989). *Schizosaccharomyces pombe* YPT1 gene coding for a small GTP binding protein was cloned using the yeast gene SEC4 as a probe (Fawell et al., 1989) and the mammalian counterpart of YPT1 was shown to be part of the secretory machinery using antibodies against the yeast Ypt1 protein (Segev et al., 1988). Mammalian rab1 protein shown to be homologous to Ypt1p (Zaraoui et al., 1989) can substitute for yeast Ypt1 function (Haubruck et al., 1990).

Genes homologous on the protein level to the yeast SSO1 and SSO2 genes according to the invention are found in several species including mouse (Hirai et al., 1992), rat (Inoue et al., 1992, Bennett et al., 1992) and nematode (Aalto et al., 1993; EMBL Data Bank 29, accession number M 75825) indicating that the genes are conserved during evolution. The homologous proteins in the other species also appear on the cell surface or are implicated to be involved in synaptic vesicle transport to the cell surface, suggesting that they may be functionally related to SSO and SSO2. However, direct involvement in secretion has only been demonstrated for the Sso-proteins, reported by us (Aalto et al., 1993). Yeast homologues for the synaptic vesicle membrane proteins, synaptobrevins are the Snc1 and Snc2 proteins (Gerst et al. 1992; Protopopov et al. 1993).

The above examples, many more of which exist, illustrate the universal nature of the secretory machinery. Results obtained with yeast are largely applicable to other fungi as well as other eukaryotic cells.

Genes with sequence similarity to the SSO genes are implicated to function also in other steps of intracellular protein transport/secretion: SED5 (Hardwick and Pelham, 1992) between ER and Golgi and PEP12 (Becherer and Jones, 1992) between Golgi and vacuole, the lysosome compartment of yeast. This further supports the central and conserved role of the SSO genes in protein secretion and intracellular transport. However, no reports exist so far on any positive effect of the SSO-homologues in yeast or animal cells on secretion when overexpressed, which effect we are showing in this invention for the SSO genes.

Less is known about the secretory system of other yeasts such as Kluyveromyces, Pichia, Schizosaccharomyces and Hansenula, which, however, have proven useful hosts for production of foreign proteins (Buckholz and Gleeson, 1991). The genetics and molecular biology of these yeasts are not as developed as for Saccharomyces but the advantages of these yeasts as production hosts are the same as for Saccharomyces. This holds true also for filamentous fungi such as Neurospora, Aspergillus and Trichoderma which have been used for production of secreted foreign proteins (Jeenes et al., 1991). Belonging taxonomically to Fungi and very many of the filamentous fungi even belonging to Ascomycetes, like S. cerevisiae does, it is evident that the secretory machinery of filamentous fungi is similar to that of S. cerevisiae. Filamentous fungi are very efficient in secreting their own hydrolytic enzymes. However, production of foreign proteins in filamentous fungi is much less efficient and in many cases this seems to be due to inefficient secretion. The common features of all fungi are for instance post-translational modifications occurring along the secretory pathway.

Several attempts have been made and published previously to increase foreign protein production in yeast and filamentous fungi as well as in other organisms. Much work has been devoted to various promoter and plasmid constructions to increase the transcription level or plasmid copy number (see e.g. Baldari et al. 1987; Martegani et al 1992; Irani and Kilgore, 1988). A common approach to try and increase secretion is to use yeast signal sequences (Baldari, et al. 1987, Vanoni et al. 1989). Random mutagenesis and screening for a secreted protein (Smith et al., 1985; Sakai et al., 1988; Schuster et al., 1989; Suzuki et al., 1989; Sleep et al., 1991; Lamsa and Bloebaum, 1990; Dunn-Coleman et al., 1991) or fusion of the foreign protein to an efficiently secreted endogenous protein (Ward et al., 1990; Harkki et al., 1989; Nyyssönen et al. 1993; Nyyssönen et al., Pat. Appl.) have been widely used both for yeast and filamentous fungi in order to make the secretion of foreign proteins more efficient. Both of these methods are of limited use. Overproduction mutants isolated by random mutagenesis and screening are almost exclusively recessive and thus cannot be transferred into industrial yeast strains which are polyploid. Often the overproduction results from changes other than increased secretion and in many cases affects only the protein used for screening. Fusion protein approach requires tailoring of the fusion construction for each foreign protein separately.

Our approach, increasing the copy number of genes functioning in secretion and thus the amount of components of the secretory machinery is more universal: it is applicable to any protein without specific fusion constructions and applicable to diploid and polyploid strains.

It is not exactly known which steps form the bottle necks in the secretory process, but it can be anticipated that there are several ones of them. We started to unravel the potential blocks at the very end of the secretory pathway, and have cloned and characterized genes participating at the very final stage of the secretory process at which the secretory vesicles budding from the Golgi complex are targetted to and fused with the plasma membrane to release the secreted proteins to the cell exterior. We have previously cloned and characterized SEC1 functioning at this stage (Aalto et al., 1991; Aalto et al., 1992) and have later shown that SEC1 is an essential single copy gene (Aalto et al., 1993). The SSO genes according to the invention were cloned as multicopy suppressors of se1-1 mutation (Aalto et al., 1993).

SUMMARY OF THE INVENTION

The present invention describes the isolation of genes which, when overexpressed enhance the production of secreted proteins. Specifically, the present invention describes the isolation of SSO1 and SSO2 genes of S. cerevisiae coding for Sso1p and Sso2p, respectively, the characterization of the genes and their transfer into, and overexpression in S. cerevisiae. In addition, this invention describes isolation of a SSO homologue from Trichoderma reesei, characterization of the gene, and transfer and overexpression in Trichoderma.

Furthermore, the sequence homologies between the yeast SSO genes and their higher eukaryotic counterparts indicates that this invention can be used to construct novel cell lines for higher eukaryotes with increased secretion capacity.

This invention thus provides new recombinant eukaryotic cells, preferably fungal host cells expressing enhanced levels of Sso protein(s), and especially yeast strains expressing enhanced levels of Sso1 and/or Sso2 proteins as well as Trichoderma strains expressing enhanced levels of Trichoderma Sso-protein. This invention also provides process(es) for production of increased amounts of secreted proteins by overexpressing genes interacting with the SSO genes, such as SEC1.

The eukaryotic cells according to the invention being transformed with the SSO genes or genes interacting with the SSO genes have an increased capacity to produce secreted proteins. The new eukaryotic cells according to the invention, especially yeast and filamentous fungi, can also be used for more efficient production of hydrolytic enzymes and hydrolysis of e.g. polymeric substrates which results in improvements in biotechnical processes such as single cell or baker's yeast production due to increased cell mass or in other processes where efficient production of hydrolytic enzymes and/or efficient hydrolysis of plant material is beneficial.

DETAILED DESCRIPTION OF THE INVENTION

Figure 1A:
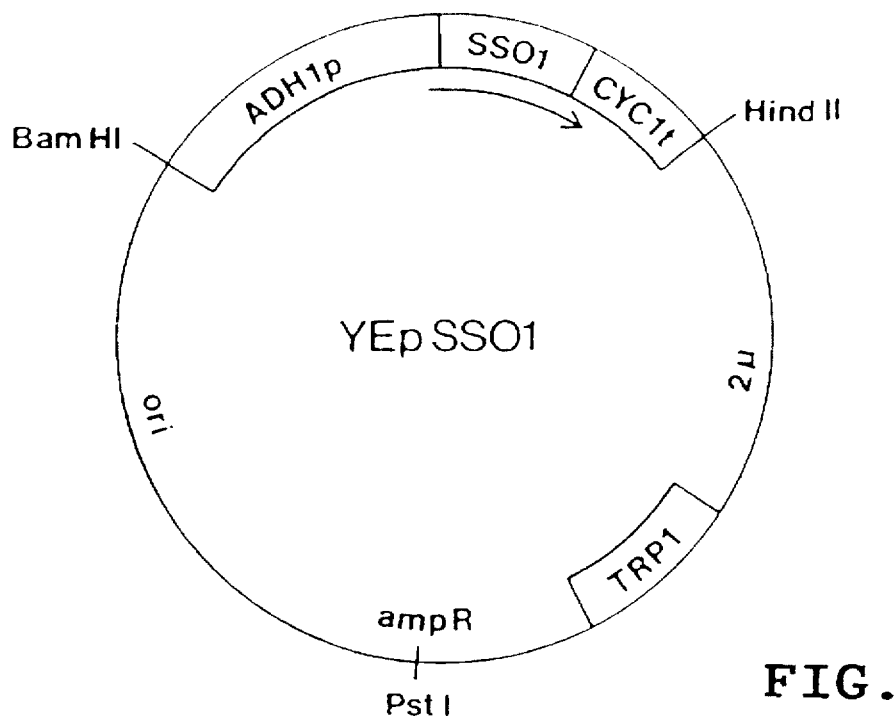
FIGS. 1A and 1B show the S. cerevisiae SSO1 and SSO2 gene cDNA integrated into a multicopy plasmid pMAC561 resulting in plasmids YEpSSO1 and YEpSSO2, respectively.

For better understanding of the following detailed description of the invention it may be helpful to give definitions of certain terms to be used hereinafter.

Overexpression of a gene: The protein encoded by the said gene is produced in increased amounts in the cell. This can be achieved by increasing the copy number of the gene by introducing extra copies of the gene into the cell on a plasmid or integrated into the genome. Overexpression can also be achieved by placing the gene under a promoter stronger than its own promoter. The amount of the protein in the cell can be varied by varying the copy number of the gene and/or the strength of the promoter used for the expression.

Suppression of a mutation: When the effect of a mutation in a given gene is alleviated or abolished by a mutation in an other gene, this second gene is called a suppressor of the first gene. Suppression can occur also by overexpression of the wild type allele of the second gene by the means described above. This is called overexpression suppression. If the overexpression is caused by multiple copies of the suppressing gene the suppression can also be called multicopy suppression. Suppression phenomenon indicates that these two genes interact at genetic level. The interaction may also occur at physical level as direct, physical contact between the two proteins encoded by the interacting genes.

Homologous genes, homologues: Genes which are related, but not identical, in their DNA sequence and/or perform the same function are homologous with each other and are called each other's homologues.

Secreted proteins: Proteins which inside of the cell are directed to the secretory pathway and transported through it to the exterior of the cell, outside of the plasma membrane, are called secreted proteins. In yeast the proteins may remain associated with the cell wall such as invertase or released through the cell wall into the growth medium such as the foreign protein Bacillus α-amylase.

SSO1 and SSO2 genes to be used in this invention are isolated from an organism containing these genes e.g. *Saccharomyces cerevisiae* and Trichoderma spp. Also other suitable yeasts and other fungi, such as *Schizosaccharomyces pombe, Kluyveromyces lactis*, Pichia spp., Hansenula spp., Aspergillus spp., Neurospora spp. and Penicillium spp. can be used. It is to be noted that homologous genes from other organisms can also be used.

Furthermore, overexpression of other genes functioning at the same step with the SSO genes, such as SEC1, in the presence of normal or increased levels of Sso-proteins results in increased secretion. Genes functioning at the preceding steps of the secretory process may well have a similar effect. Thus, release of the secretory vesicles from the Golgi compartment may be facilitated by increasing the copy number of SEC7 and/or SEC14 genes known to function at this step (Novick et al. 1980) or by searching for and increasing the copy number of genes interacting with SEC7 and/or SEC14 e.g. suppressors of their mutations. Likewise any previous step of the secretory process may be improved by increasing the copy number of genes involved. The new genes we have isolated from *S. cerevisiae*, SSO1 and SSO2 represent duplicated genes which suggests that they play an important role in the cell. Based on the conserved nature of SSO1 and SSO2 and their homologues in other species, as mentioned above, we propose that increase of the SSO genes in any other eukaryotic species would result in increased protein secretion efficiency including other yeasts, filamentous fungi, and plant and animal cells.

It is to be noticed that due to the fact that many genes involved in secretion function in other organisms, this invention covers for instance also expression of yeast genes in filamentous fungi and higher eukaryotes and vice versa, or any eukaryotic gene in another eukaryote to obtain enhanced secretion.

The host to be transformed with the genes of the invention can be any eukaryotic cell suitable for foreign or endogenous protein production, e.g. any *S. cerevisiae* yeast strain, (e.g. DBY746, AH22, S150-2B, GPY55-15Ba, VTT-A-63015) any Trichoderma spp. such as *T. harzianum* and the *T. reesei* strains derived from the natural isolate QM6a, such as RUTC-30, QM9416 and VTT-D-79125, any Kluyveromyces spp., *Sch. pombe, H. polymorpha*, Pichia, Aspergillus, Neurospora, Yarrowia, Penicillium spp. or higher eukaryotic cells. Transfer of the genes into these cells can be achieved, for instance, by using the conventional methods described for these organisms.

The DNA sequence containing SSO1 or SSO2 is isolated from *S. cerevisiae* by conventional methods. In a preferred embodiment gene or cDNA library on a multicopy plasmid is used to suppress the temperature-sensitivity of sec1-1 mutant (Aalto et al., 1991; 1993) or mutations leading to deficiency in the SSO function of *S. cerevisiae* or analogous mutations of other species. In another approach the known DNA sequence of the SSO genes and SSO-like genes is used to design probes for heterologous hybridization or PCR primers for cloning the SSO genes. In still another approach antibodies to the known SSO and SSO-like genes are used for cloning the gene by standard methods.

The genes corresponding to the *S. cerevisiae* SSO1 and SSO2 are isolated from the other fungi or higher eukaryotes with one or several of the following methods, which are here described specifically for the filamentous fungus *Trichoderma reesei* and which can be modified according to conventional knowledge and means to suit the eukaryotic cell in question.

A cDNA bank of *T. reesei* is constructed into the yeast vector pFL60 as described in the FI patent application No. 92 2373 (Buchert et al.). This gene bank DNA is transformed into the S.cerevisiae strain H458 (Aalto et al., 1993) and screened for complementation of the secretion defect e.g. as described in Example 6. The plasmid is isolated from the positive colonies and the gene is isolated and characterized using standard methodology, and the corresponding chromosomal gene is isolated. Succesful complementation shows that functionally equivalent genes to the yeast SSO genes exist in other fungi such as T. reesei.

Alternatively, the genes encoding proteins corresponding to the S. cerevisiae Sso1p and/or Sso2p can be isolated from a cDNA or a chromosomal gene bank prepared from T. reesei by heterologous hybridization in non-stringent conditions as described in Example 7 and characterized by conventional methods and their function can be shown as described above. Similar approach is suitable for all organisms which have shown to possess chromosomal sequences homologous to the yeast SSO genes as analyzed for instance by Southern hybridization of total DNA. It is also possible that the gene can be isolated from an expression library with antibodies prepared against the yeast Sso proteins.

Alternatively, oligonucleotide primers can be designed based on the homologies found between the sequences of the corresponding genes isolated from several organisms. Clear homologies are seen for instance in regions extending from aa 266 to aa 287 in Sso1p and from aa 269 to aa 290 in Sso2p, shown in SEQ ID NO. 1 and SEQ ID NO. 3, respectively. These primers are used to amplify the T. reesei gene in a PCR reaction.

To construct a plasmid suitable for transformation into a yeast, the SSO1 or SSO2 gene is cloned into a suitable yeast expression vector, such as pAAH5 (Ammerer, 1983) or vectors derived from it (Ruohonen et al., 1991; Ruohonen et al., manuscript in preparation, a) comprising the appropriate yeast regulatory regions. These regulatory regions can be obtained from yeast genes such as the ADH1, GAL1–GAL10, PGK1, CUP1, GAP, CYC1, PHO5, or asparagine synthetase gene, for instance. Alternatively, also the regulatory regions of SSO1 or SSO2 can be used to express the genes in S. cerevisiae. The plasmid carrying the SSO1 or SSO2 gene is capable of replicating autonomously when transformed into the recipient yeast strain. The gene SSO1 or SSO2 together with the appropriate yeast regulatory regions can also be cloned into a single copy yeast vector such as pHR70 of Hans Ronne or pRS313, pRS314, pRS315 or pRS316 (Sikorski and Hieter, 1989).

Figure 7:
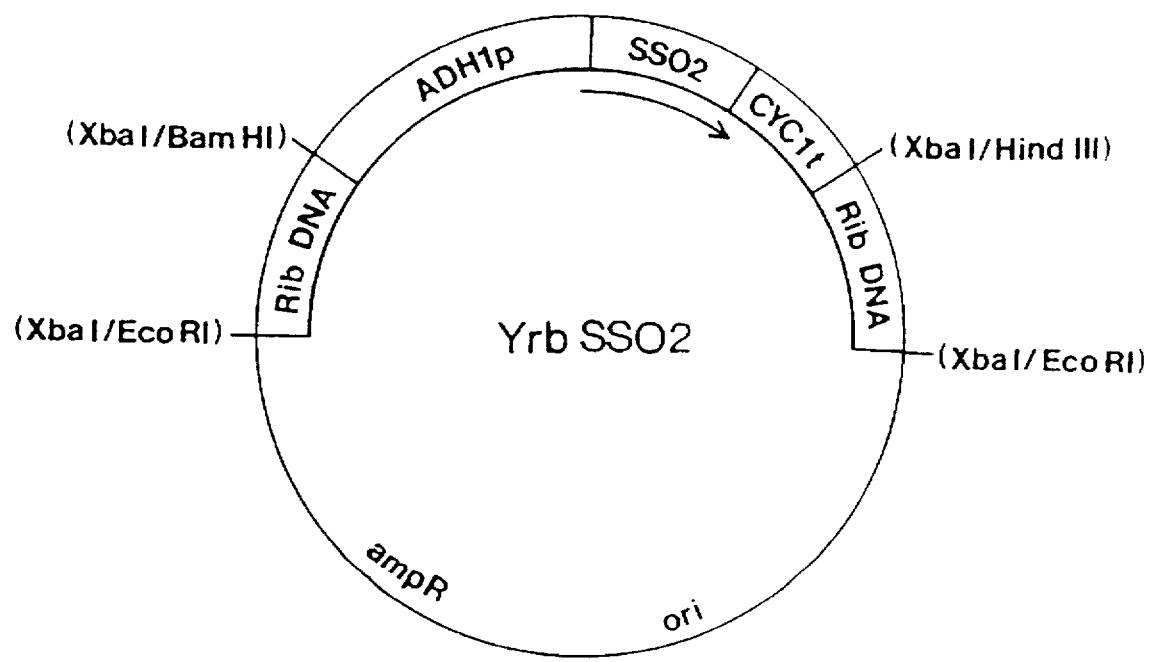
FIG. 7 shows the SSO2 expression cassette flanked by ribosomal sequences integrated into BS+, generating the vector pRbSSO2.

Alternatively, extra copies of SSO1 or SSO2 gene can also be integrated into the yeast chromosome, into the ribosomal RNA locus, for instance. For this purpose the ribosomal sequences of a suitable plasmid, e.g. plasmid pIRL9 (Hallborn et al., Pat. Appl.) are released, and cloned appropriately into BS+ vector, as shown in FIG. 7. The gene SSO1 or SSO2 coupled in between suitable yeast promoter and terminator regions, is released from the hybrid vector comprising the gene and cloned into the plasmid obtained at the previous stage. From this resulting plasmid the expression cassette, flanked by ribosomal sequences can be released. This fragment is cotransformed into a yeast with an autonomously replicating plasmid carrying a suitable marker for transformation. The plasmid can be later on removed from the cells containing the extra copies of SSO1 or SSO2 gene integrated in the chromosome by cultivating the cells in non-selective conditions. This way, recombinant strains can be obtained which carry no extra foreign DNA such as bacterial vector sequences. If a polyploid yeast strain, such as VTT-A-63015, is used the gene can be integrated also to an essential locus such as the ADH1 or the PGK1 locus.

To express the SSO genes in Trichoderma the coding region of the Trichoderma sso gene is coupled for instance between the T. reesei cbh1 promoter and terminator and the expression cassette is transformed into a Trichoderma strain producing for instance mammalian antibodies or another foreign protein or into a strain producing EGIcore, another cellulase or a hydrolytic enzyme. Enhancement of secretion would be especially desired when the fungus is grown on glucose-containing media and for this purpose the sso gene (s) need to be expressed from constitutive promoters or promoters functioning on glucose medium.

For filamentous fungi the sso gene is preferably integrated into the genome using methods known in the art. Suitable promoters in addition to the cbh1 promoter or promoter of the sso gene itself are for instance the other cellulase promoters, cbh2, egl1, egl2, or tef1, pgk, gpd, pki, the glucoamylase, α-amylase or the alcohol dehydrogenase promoter. In filamentous fungi transformation usually results in strains with varying copies of the sso gene integrated into the genome (Penttilä et al., 1987) and from these the strain with optimal level of sso expression for growth and enhanced secretion can be screened.

An object of this invention is thus to provide SSO genes, especially the SSO1 and SSO2 genes of S. cerevisiae, as well as homologous gene(s) of Trichoderma reesei and other eukaryotic cells. The sequence of the genes can be determined from the plasmids carrying them by using e.g. the double stranded dideoxy nucleotide sequencing method (Zagursky et al., 1986). The sequence of the SSO1 gene of S. cerevisiae is given as the SEQ ID NO. 1 and the sequence of the SSO2 gene of S. cerevisiae is given as the SEQ ID NO. 3.

Another object of this invention is to provide specific vectors comprising the SSO genes. For yeast such a vector is either an autonomously replicating multicopy or a single copy plasmid or a vector capable of integrating into the chromosome, as described above. For Trichoderma such a vector is preferably a plasmid from which the expression cassette (promoter-gene-terminator) can be released by restriction enzymes to be integrated into the fungal genome.

Still another object of this invention is to provide yeast or other fungal strains as well as eukaryotic cell lines containing extra copies of SSO genes either on replicating plasmid (s) or integrated into the chromosomes, which results in increased production of secreted proteins, such as yeast invertase or Trichoderma cellulases or other hydrolases.

Thus a method for constructing new eukaryotic cells capable of expressing enhanced levels of Sso protein(s) comprises:

(a) isolating DNA sequence(s) coding for Sso protein(s) from a suitable donor organism;

(b) constructing vector(s) carrying at least one of the said DNA sequences; and (c) transforming at least one of the vectors obtained to suitable host cells.

Still another object of this invention is to provide eukaryotic cells which in addition to extra copies of SSO genes comprise a DNA sequence coding for a secreted foreign or endogenous protein, such as α-amylase, cellulase, or an antibody and are capable of expressing this protein.

Thus a process for producing increased amounts of secreted foreign or endogenous protein(s) by overexpressing the SSO gene(s) is provided. This process comprises:

(a) isolating DNA sequence(s) coding for the said protein (s) from a suitable donor organism;

(b) constructing a vector carrying at least one of the said DNA sequences;

(c) transforming the vector obtained into a suitable host expressing enhanced levels of Sso protein(s) to obtain recombinant host cells; or alternatively, transforming the vector to a suitable host and retransforming this transformant with SSO or a gene homologous to SSO and screening for cells with enhanced production of the said protein(s); and (d) cultivating said recombinant host cells under conditions permitting expression of said protein(s).

A further object of this invention is to improve secretion by optimizing the Sso-protein level using different promoters and different copy numbers of the gene and combining the SSO genes with other genes involved in secretion, such as SEC1.

Thus the invention provides a process for producing increased amounts of secreted foreign or endogenous protein (s), by overexpressing gene(s) interacting with the SSO gene, e.g. SEC1, in the presence of normal or increased amounts of the Sso protein(s), which process comprises:

(a) isolating DNA sequence(s) coding for the said protein (s) from suitable donor organism;

(b) constructing a vector carrying at least one of the said DNA sequences;

(c) transforming the vector obtained into a suitable host expressing normal or enhanced levels of Sso protein(s) and overexpressing other gene(s) interacting with SSO gene, e.g. SEC1, to obtain recombinant host cells; or, alternatively, transforming the vector to a suitable host and retransforming this transformant with SSO or a gene homologous to SSO and by the gene interacting with SSO gene and screening for cells with enhanced production of the said protein(s); and (d) cultivating said recombinant host cells under conditions permitting expression of said protein(s).

Still another object of this invention is to provide a process for increased production of an endogenous secreted protein, the process comprising:

(a) transforming cells producing the said protein with a SSO gene or a gene homologous to SSO, alone or together with gene(s) interacting with the SSO gene, such as SEC1, (b) screening for transformants producing enhanced level of the said protein thus obtaining recombinant cells for enhanced protein production, and (c) cultivating said recombinant cells in conditions permitting expression of said protein.

Still another object of this invention is to provide fungal strains which in addition to extra copies of SSO genes or their homologue comprise DNA sequence(s) coding for hydrolytic enzyme(s) such as α-amylase and/or glucoamylase or lignocellulose hydrolyzing enzymes such as cellulase (s), hemicellulases or ligninases, which render the fungus capable of increased hydrolysis of, and/or enhanced growth on polymeric compounds such as starch or lignocellulose.

Thus an efficient biomass production on said raw material or efficient hydrolysis of said raw material is provided. This process comprises:

(a) isolating DNA sequence(s) coding for endogenous or foreign hydrolytic enzyme(s) from a suitable donor organism;

(b) constructing a fungal vector carrying at least one of the said DNA sequences;

(c) transforming the vector obtained into a suitable fungal host expressing enhanced levels of Sso protein(s) to obtain recombinant host cells; or alternatively, transforming the vector to a suitable host and retransforming this transformant with SSO or a gene homologous to SSO and screening for cells with enhanced production of the said enzyme(s); and (d) cultivating said recombinant host cells under conditions permitting expression of said hydrolytic enzyme (s).

A process is also provided for efficient biomass production on a raw material or efficient hydrolysis of a raw material, by overexpressing genes interacting with the SSO gene, e.g. SEC1, in the presence of normal or increased amounts of the Sso protein(s). This process comprises:

(a) isolating the DNA sequence(s) coding for endogenous or foreign hydrolytic enzyme(s) from a suitable donor organism;

(b) constructing a vector carrying at least one of the said DNA sequences;

(c) transforming the vector obtained to a suitable host expressing enhanced levels of proteins interacting with the Sso protein(s) in the presence of normal or increased amounts of the Sso protein(s) to obtain recombinant host cells, or, alternatively, transforming the vector to a suitable host and retransforming this transformant with SSO gene or a gene homologous to SSO and with the gene(s) interacting with SSO gene, such as SEC1, and screening for cells with enhanced production of the said enzyme(s); and (d) cultivating said recombinant host cells under conditions permitting expression of said hydrolytic enzyme (s).

Possible applications of said recombinant cells are e.g. in single cell production, improved alcohol production or in processes where efficient hydrolysis of raw material is desired.

EXPERIMENTAL

EXAMPLE 1

Cloning of the Coding Region of SSO1 and SSO2 Genes From *Saccharomyces cerevisiae*

The SSO1 and SSO2 genes were isolated as suppressors of the temperature-sensitive defect of sec1-1 mutant (Novick and Scheckman, 1979; Novick et al., 1980). The *S. cerevisiae* strain sf750-14Dα (α sec1-1 his4 ura3-52 trp1-289 leu2-3 leu2-112) (obtained from Randy Scheckman, University of California, Berkeley, Calif.) was transformed (Ito et al., 1983) by yeast cDNA library constructed by McKnight and McConaughy (1983) from strain X2180-1B on a 2μ based plasmid, pMAC561, containing 7P1 as a selection marker, and selected for Trp-prototrophy at 37° C. As the growth of the transformnants was refractory at 37° C., further work was done at 36.5° or 35° C. temperatures which still are non-permissive for sec1-1. DNA isolated (Keränen, 1986) from four yeast transformants which showed co-segregation of the Trp$^+$ phenotype and growth at 36.5° C. was transferred into *E. coli* (Hanahan, 1983). Plasmid DNA isolated from *E. coli* transformants was used to re-transform the sec1-1 strain of *S. cerevisiae*.

Figure 1B:
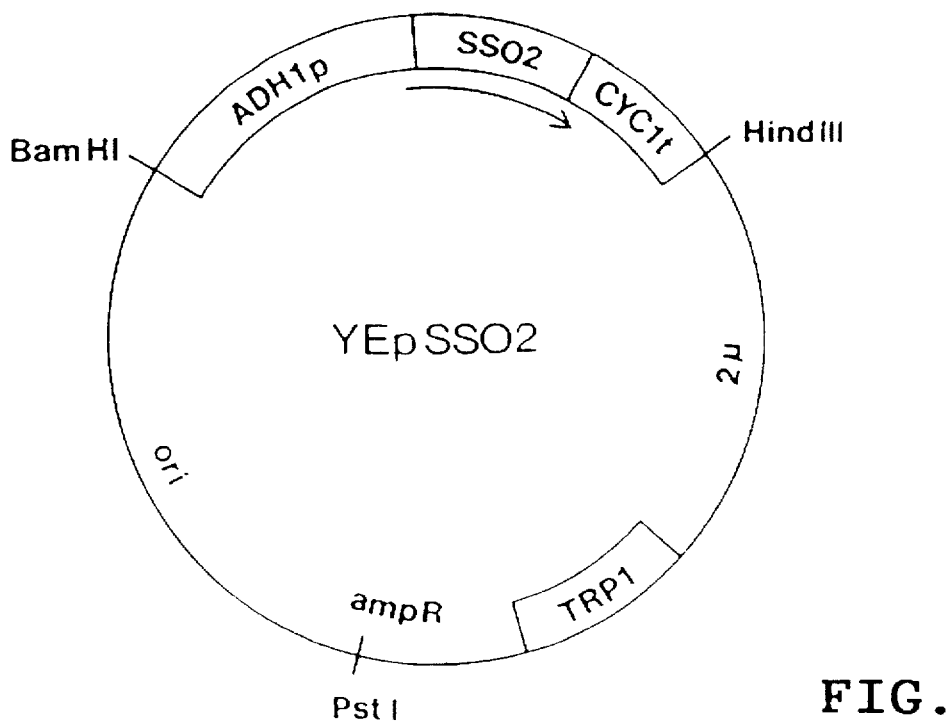

Efficient transformation for growth at 36.5° C. was obtained. Restriction enzyme analysis of the plasmids indicated that two different sequences were recovered from the cDNA library used. The insert DNA from the two different clones, 1 and 7, was sequenced using the double stranded dideoxy method (Zagursky et al., 1986) and suitable subclones constructed with standard recombinant DNA methods (Maniatis et al., 1982) or specific primers. The two clones contained an open reading frame of 870 nucleotides (clone 1) and 885 nucleotides (clone 7), respectively. As the deduced amino acid sequences did not represent that of the Sec1 protein (Aalto et al., 1991) the new genes were named SSO1 and SSO2 (Suppressor of Sec1 One). The SSO1 and SSO2 coding sequences and the deduced amino acid sequences are given in SEQ ID NO: 1 and SEQ ID NO: 3, respectively. The plasmids carrying the SSO1 and SSO2 genes were named YEpSSO1 and YEpSSO2, respectively and are shown in FIGS. 1A and 1B.

EXAMPLE 2

Overexpression of the Sso2 Protein in Yeast Transformed with YEpSSO2

Figure 2:
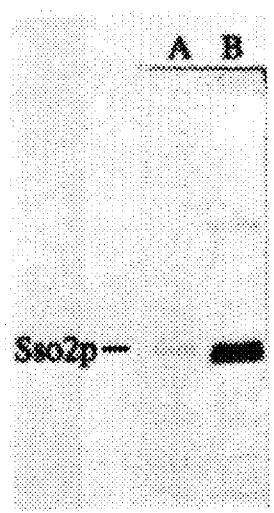
FIG. 2 shows Western analysis demonstrating overexpression of Sso2 protein in yeast transformed with YEpSSO2.

The yeast strain sf750-14D transformed with the control plasmid pMA56 (A) (Ammerer, 1983) or with YEpSSO2 (B) were grown in synthetic complete medium (Sherman et al. 1983) lacking Trp. Yeast cell lysates were prepared in the presence of SDS as described by Keränen (1986). Ten µg of total yeast protein present in the lysates were separated by SDS-PAGE and analyzed by Western blotting using polyclonal antibodies made in rabbit against the Sso2 protein and alkaline phosphatase conjugated goat anti-rabbit IgG for detection. As shown in FIG. 2, greatly increased amount of Sso2 protein was seen in the YEpSSO2 transformant.

EXAMPLE 3

Enhanced Production of Secreted Heterologous Protein, Bacillus α-amylase in Yeast Strain sf750-14D Overexpressing either SSO1 or SSO2

Figure 3:
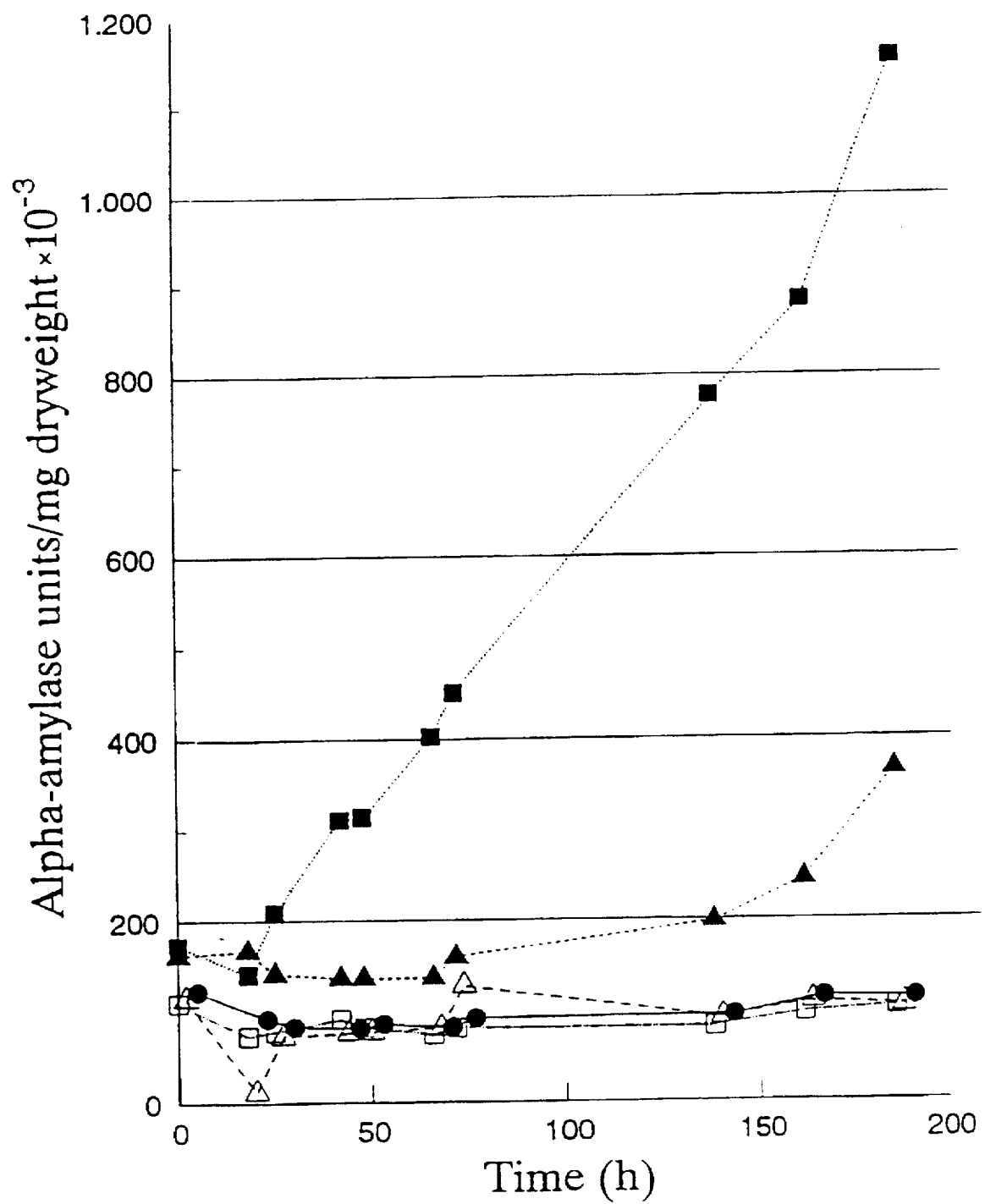
FIG. 3 shows increased production of secreted Bacillus α-amylase by *S. cerevisiae* (strain sf750-14D) transformed with multicopy plasmid, expressing SSO1 or SSO2 gene and with another plasmid expressing Bacillus α-amylase gene.
Figure 4:
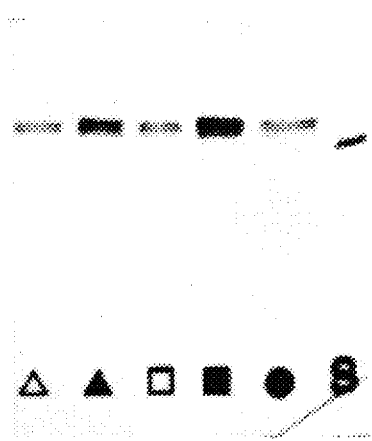
FIG. 4 shows Western analysis of Bacillus α-amylase secreted by *S. cerevisiae* with or without the multicopy plasmid expressing SSO1 or SSO2 gene.

The yeast strain sf750-14Dα harboring either SSO1 or SSO2 gene on the multicopy plasmids YEpSSO1 or YEpSSO2, respectively, were transformed with a multicopy plasmid Yepαa5 containing Bacillus α-amylase gene ligated between the ADH1 promoter and terminator (Ruohonen et al., 1987), modified for more efficient expression by deleting predicted inhibitory sequences 5' to the promoter element (Ruohonen et al., 1991; Ruohonen et al., manuscript in preparation, a). The yeast strains obtained containing YEpSSO1 and YEpαa5 (VTT-C-92072) or YEpSSO2 and YEpαa5 (VTT-C-92073) were grown in selective medium at 24° C. and secretion of α-amylase into the culture medium was monitored by measuring the α-amylase activity using the Phadebas amylase test (Pharmacia Diagnostics AB, Sweden). These strains VTT-C-92072 and VTT-C-92073 were deposited at the Deutsche Sammlung von Mikroorganismen und Zellkulturen GmbH (DSM) on 30 September 1992 with the accession numbers DSM 7253 and 7254, respectively. As shown in FIG. 3, increased α-amylase activity was obtained in strains which carried either SSO1 (▲) or SSO2 (■) on the multicopy plasmid compared with the untransformed control strain (●). Segregation of YEpSSO1 (△) or YEpSSO2 (□) off from the transformants reduced the α-amylase secretion to the control level proving that the increased secretion is due to the presence of the SSO gene containing plasmids in the transformants. Increased amount of α-amylase protein in the culture medium was detected by Western blotting (FIG. 4). Symbols as for FIG. 3., S=standard (Bacillus α-amylase).

EXAMPLE 4

Enhanced Production of Secreted Foreign Protein, Bacillus α-amylase and an Endogenous Protein, Invertase in Yeast Strain DBY746 Overexpressing SSO2

Figure 5:
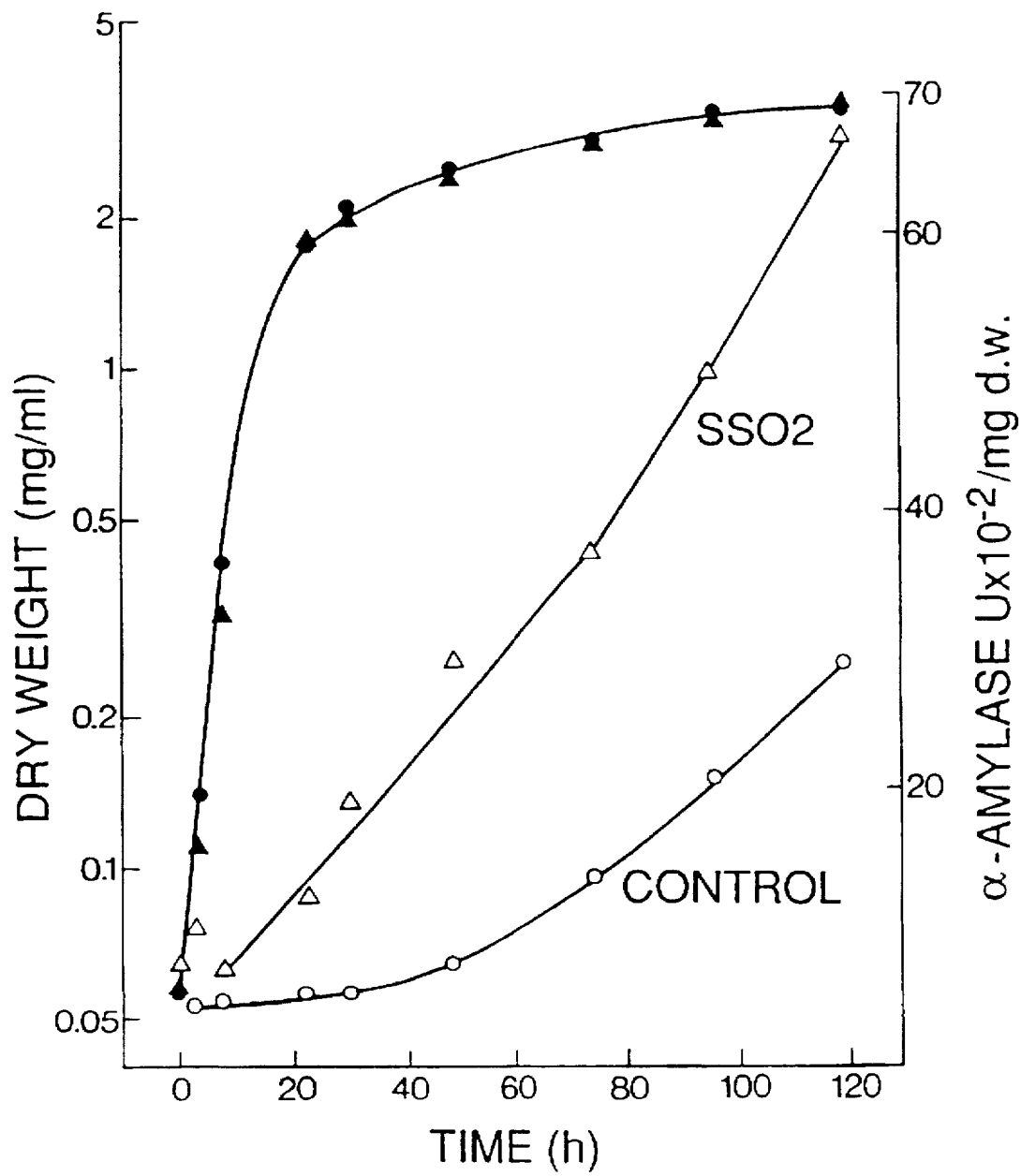
FIG. 5 shows increased production of secreted Bacillus α-amylase by *S. cerevisiae* (strain DBY746) transformed with multicopy plasmid, expressing SSO2 gene and with another plasmid expressing Bacillus α-amylase.

The *S. cerevisiae* strain DBY746 (α his3Δ1 leu2-3 leu2-112 ura3-52 trp1-289 cgh$^R$) (obtained from David Botstein, Department of Biology, Massachusetts Institute of Technology, Cambridge, Mass.) harboring the plasmid YEpαa6 containing Bacillus α-amylase gene ligated between the ADH1 promoter and terminator (Ruohonen et al., 1987), modified for more efficient expression by deleting predicted inhibitory sequences 5' to the promoter element (Ruohonen et al., 1991; Ruohonen et al., manuscript in preparation, a) was transformed either with YEpSSO2 or with the control plasmid pMA56 (Ammerer, 1983). The transformants were grown in selective medium at 30° C. and secretion of α-amylase into the culture medium was monitored by measuring the α-amylase activity using the Phadebas amylase test (Pharmacia Diagnostics AB, Sweden). As shown in FIG. 5, increased α-amylase activity was obtained in the strain which carried SSO2 (△) on the multicopy plasmid compared with the control strain transformed with the control plasmid without SSO gene (○).

No difference was observed in the yeast growth between the control transformant (●) and SSO2 transformant (▲). Overexpression of SSO1 increased the secretion of α-amylase in a similar manner. Secretion of the endogenous protein, invertase, was also enhanced under these conditions measured at late logarithmic to early stationary growth phase. The secreted invertase activity in the YEpSSO2 transformant was 1.4 times that in the control transformant containing pMA56. As the enhancing effect of SSO overexpression on α-amylase secretion is more pronounced later during the growth, also the invertase secretion should be more enhanced at later time points.

Removal of the predicted inhibitory sequences on the ADH1 promoter (see above) used for expression of the SSO2 in YEpSSO2 resulted in prolonged expression of SSO2 and prolonged existence of increased level of the Sso2 protein and consequently even higher final levels of the Bacillus α-amylase secreted into the medium. Expression of SSO2 on a single copy plasmid from this modified ADH1 promoter also resulted in increased levels of the Sso2 protein and enhanced secretion of α-amylase.

EXAMPLE 5

Figure 6:
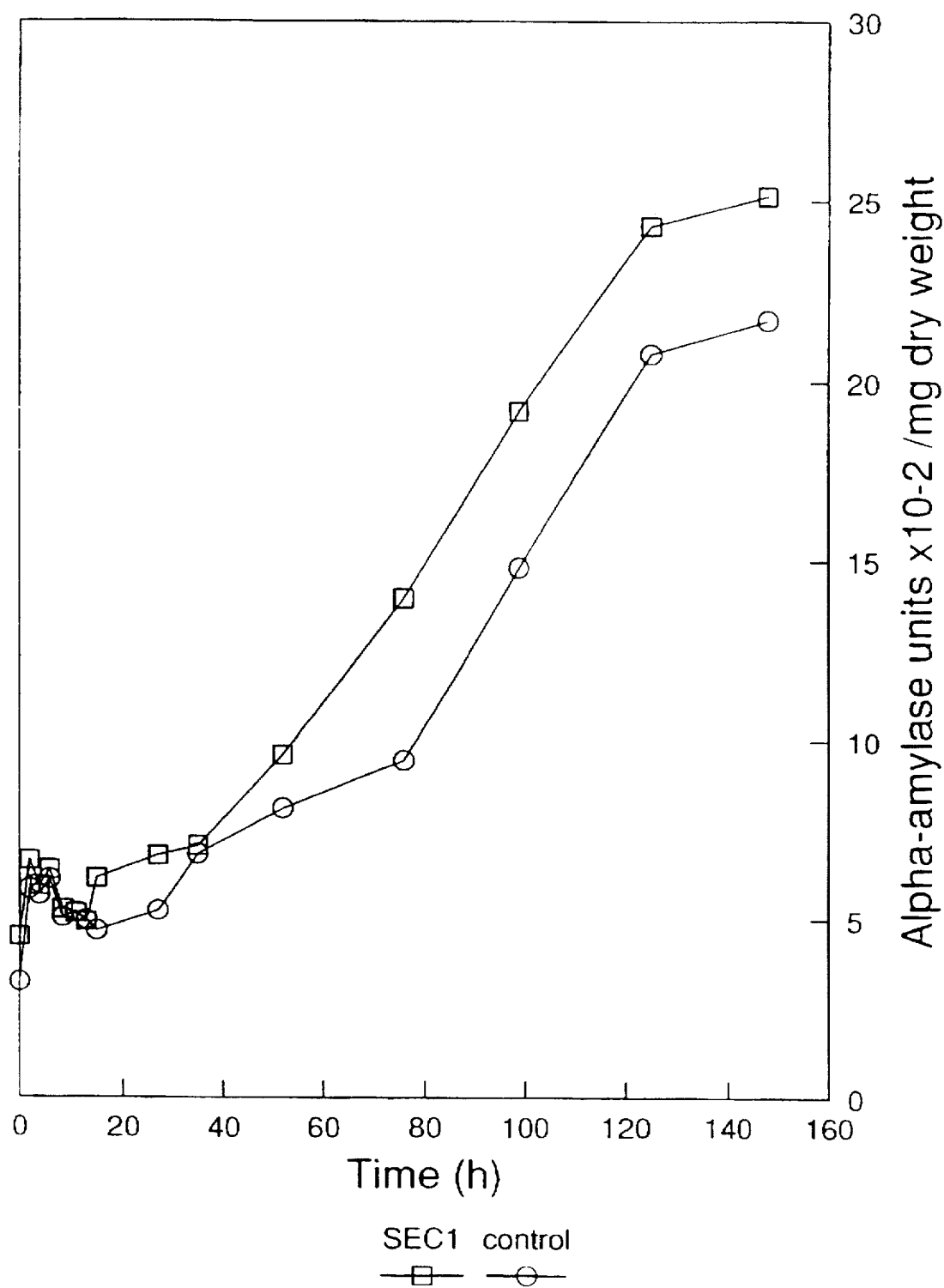
FIG. 6 shows increased production of secreted Bacillus α-amylase by *S. cerevisiae* (strain DBY746) transformed with a multicopy plasmid expressing SEC1 gene and with another plasmid expressing Bacillus α-amylase.

Enhanced Production of Secreted Foreign Protein, Bacillus α-amylase in Yeast Overexpressing SEC1 in Combination with Normal or Increased Levels of Functional Sso Proteins The *S. cerevisiae* strain DBY746 harboring the plasmid YEpαa6 containing Bacillus α-amylase gene ligated between the ADH1 promoter and terminator (Ruohonen et al., 1987), modified for more efficient expression by deleting predicted inhibitory sequences 5' to the promoter element (Ruohonen et al., 1991; Ruohonen et al., manuscript in preparation, a) was transformed either with a multicopy plasmid YEpSEC1 expressing the SEC1 gene or with the control plasmid YEp24H (Aalto et al., 1991; Ruohonen et al., manuscript in preparation, b). The transformants were grown in selective medium at 30° C. and secretion of α-amylase into the culture medium was monitored by measuring the α-amylase activity using the Phadebas amylase test (Pharmacia Diagnostics AB, Sweden). As shown in FIG. 6, increased α-amylase activity was obtained in the strains which carried SEC1 on a multicopy plasmid (□) compared with the strains transformed with the vector without SEC1 gene (○). No difference was observed in the growth between the transformants.

Overexpression of both Sec1p and Sso2p at the same time enhanced α-amylase secretion even further. The plasmids expressing the SSO genes are available at VTT, Biotechnical Laboratory, Espoo, Finland.

EXAMPLE 6

Isolation of the Trichoderma sso Genes by Expression in Yeast and their Expression in Trichoderma A yeast expression gene bank prepared from the *T. reesei* strain QM9414 as described (Buchert et al., FI Pat Appl. 922373) was transformed into the Saccharomyces cerevisiae strain H458 (Aalto et al., 1993) (a SUC2 ade2-1 can1-100 his3-11,15 leu2-3,112 trp1-1 ura 3-1 sso1-δ1::URA3 sso2-δ2::leu2::(GAL1:sso1,HIS3)) by selecting for Ura-prototrophy on a galactose medium The transformants were transferred onto glucose medium and the plasmid was rescued from the growing colonies and retransformed into the above mentioned strain to verify the complementation. A clone was obtained showing capability to rescue depletion of the Sso proteins on glucose medium and the corresponding plasmid was named pMS51. The *S. cerevisiae* strain obtained, carrying the plasmid pMS51 was deposited at the Deutsche Sammlung von Mikroorganismen und Zellkulturen GmbH (DSM) on 5 Oct. 1993 with the accession number DSM 8604. The chromosomal copy of the gene is isolated from a genomic cosmid library (Mäntylä et al., 1992) by using the 5' end of the cDNA clones as a probe, prepared by PCR. The cosmid is isolated from the clones giving a signal, and those corresponding to the above mentioned cDNA are transformed into a *T. reesei* (Pentilla et al., 1987) strain producing CBHI-Fab molecules VTF-D-91418 (CBS 287.91) described in Nyyssönen et al., (Pat. Appl.). Production of CBHI-Fab is studied from the extracellular medium on Solca-floc medium (according to Nyyssönen et al., Pat. Appl.).

EXAMPLE 7

Isolation of Fungal sso Genes by Heterologous Hybridization

Figure 8:
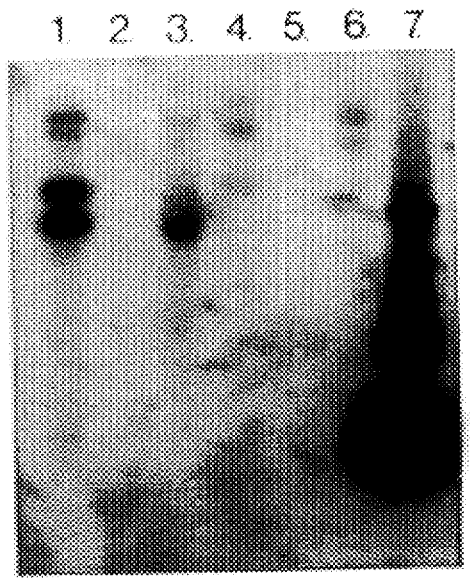
FIG. 8 shows hybridization of DNA derived from six different fungal species with the yeast SSO1 gene.

Genomic DNA from the fungal species *Saccharomyces cerevisiae*, *Schizosaccharomyces pombe*, *Kluyveromyces lactis*, *Pichia stipitis*, *Aspergillus nidulans* and *Trichoderma reesei* were isolated, digested with the HindIII restriction enzyme, separated electrophoretically in an 0.8% agarose gel and blotted on a nylon filter. Southern hybridization of the filter was carried out at different stringencies using the yeast SSO1 gene coding region as a probe. Hybridization in a mixture containing 30% formamide, 6×SSC, 10×Denhardt's, 0.5% SDS, 100 µg/ml herring sperm DNA and 10 µg/ml polyA at 35° C. and washing 2×30 minutes in 2×SSC, 0.1% SDS at 42° C. revealed several hybridizing bands in DNA derived from *S. cerevisiae*, *K. lactis*, *P. stipitis* and *T. reesei* (FIG. 8). When hybridization was performed in less stringent conditions, hybridization was observrd also with *S. pombe* DNA. A genomic *T. reesei* gene library constructed in the λEMBL3 (Frischauf et al., 1983) vector was hybridized by the procedure described above. Clones giving hybridization signals were purified and their hybridizing regions were mapped by digestions and Southern hybridizations of their DNA. The three hybridizing λ clones were designated TSSOa, TSSOb and TSSOc. These clones were deposited at the Deutsche Sammlung von Mikroorganismen und Zellkulturen GmbH (DSM) on 5 Oct. 1993 with the accession numbers DSM 8601, DSM 8602 and DSM 8603, respectively.

Deposited Microorganisms

The following microorganisms were deposited according to the Budapest Treaty at the Deutsche Sammlung von Mikroorganismen und Zellkulturen GmbH (DSM), Mascheroder Weg 1b, D-3300 Braunschweig, Germany.

| Strain | Deposition number | Deposition date |
| --- | --- | --- |
| Saccharomyces cerevisiae VTT-C-92072 carrying the plasmid YEpSSO1 | DSM 7253 | 30 September 1992 |
| Saccharomyces cerevisiae VTT-C-92073 carrying the plasmid YEpSSO2 | DSM 7254 | 30 September 1992 |
| Saccharomyces cerevisiae H458 (VTT-C-93002) carrying the plasmid pMS51 | DSM 8604 | 5 October 1993 |
| Bacteriophage λ strain TSSOa (VTT-H-93001) | DSM 8601 | 5 October 1993 |
| Bacteriophage λ strain TSSOb (VTT-H-93002) | DSM 8602 | 5 October 1993 |
| Bacteriophage λ strain TSSOc (VTT-H-93003) | DSM 8603 | 5 October 1993 |

References

Aalto, M. K., Keränen, S. and Ronne, H. 1992. A family of proteins involved in intracellular transport. Cell 68, 181–182.

Aalto, M. K., Ronne, H. and Keränen, S. 1993. Yeast syntaxins Sso1p and Sso2p belong to a family of membrane proteins that function in vesicular transport. EMBO J. 12, (in press).

Aalto, M. K., Ruohonen, L., Hosono, K. and Keränen, S. 1991. Cloning and sequencing of the yeast *Saccharomyces cerevisiae* SEC1 gene localized on chromosome IV. Yeast 7, 643–650.

Ammerer, G. 1983. Expression of genes in yeast using the ADC1 promoter. Methods Enzymol. 101, 192–201.

Baldari, C., Murray, J. A. H., Ghiara, P., Cesareni, G. and Galeotti, C. L. 1987. A novel peptide leader which allows efficient secretion of a fragment of human interleukin 1β in *Saccharomyces cerevisiae*. EMBO J., 6, 229–234.

Becherer, K. A. and Jones, E. W., 1992. Role of the PEP12 gene product in vacuolar targetting in yeast. EMBL Data Bank 31, accession number M90395.

Bennett, M. K., Calakos, N. and Scheller, R. H. 1992. Syntaxin: A synaptic protein implicated in docking of synaptic vesicles at pre synaptic active zones. Science 257, 255–259.

Buchert, J., Penttilä, M., Siika-aho, M., Saloheimo, A., Ranua, M. and Viikari, L. 1992. Mannanaasientsyymit, niitä koodittavat geenit ja menetelmä näiden erist ämiseksi sekä menetelmä lignoselluloosapitoisen massan valkaisemiseksi (Mannanase enzymes, the encoding genes and method for their isolation, and a method for bleeching lignocellulose containing materials). FI Pat. Appl. 92 2373.

Buckholz, R. G. and Gleeson, M. A. 1991. Yeast systems for the commercial production of heterologous proteins. Bio/Technology 9, 1067–1072.

Dunn-Coleman, N., Bloebaum, P., Berka, R., Bodie, E., Robinson, N., Armstrong, G., Ward, M., Przetak, M., Carter, G., LaCost, R., Wilson, L., Kodama, K., Baliu, E., Bower, B., Lamsa, M. and Heinsohn, H. 1991. Commercial levels of chymosin production by Aspergillus. Bio/Technology 9: 976–981.

Fawell, E., Hook, S. and Armstrong, J., 1989. Nucleotide sequence of a gene encoding a YPT1-related protein from *Schizosaccharomyces pombe*. Nucl. Acid Res. 11, 4373.

Frischauf, A.-M., Lerach, H., Poutstka, A. and Murray, N., 1983. Lambda replacement vectors carrying polylinker sequences. J. Mol. Biol. 170, 827–842.

Gerst, F. E., Rodgers, L., Riggs, M. and Wigler, M. 1992. SNC1, a yeast homolog of the synaptic vesicle-associated membrane protein/synaptobrevin gene family: Genetic interactions with the RAS and CAP genes. Proc. Natl. Acad. Sci. USA 89, 4338–4342.

Greenberg, G., Shelness, G. S. and Blobel, G., 1989. A subunit of mammalian signal peptidase is homologous to yeast SEC11 protein. J. Biol. Chem. 264, 15762–15765.

Hallborn, J., Penttilä, M., Ojamo, H., Keränen, S. & Hahn-Hägerdal, B. 1990. Xylose utilization by recombinant yeasts. International Pat. Appl. WO 91/15588.

Hanahan, D. 1983. Studies on transformation of *Escherichia coli* with plasmids. J. Mol. Biol. 166, 557–580.

Hardwick, K. G. and Pelham, H. R. B. 1992. SED5 encodes a 39 KD integral membrane protein required for vesicular transport between the ER and the Golgi complex. EMBL Data Bank 32, accession number X66980.

Harkki, A., Uusitalo, J., Bailey, M., Penttilä, M. & Knowles, J. K. C. 1989. A novel fungal expression system: secretion of active calf chymosin from the filamentous fungus *Trichoderma reesei*. Bio/Technology 7: 596–603.

Haubruck, H., Prange, R., Vorgias, C. and Gallwitz, D. 1989. The ras-related mouse ypt1 protein can functionally replace the YTP1 gene product in yeast. EMBO J. 8, 1427–1432.

Hirai, Y. Takebe, K., Takashina, M., Kobayashi, S. and Takeichi, M. 1992. Epimorphin: a mesenchymal protein essential for epithelial morphogenesis. Cell 69, 471–481.

Inoue, A., Obata, K. and Agakawa, K. 1992. Cloning and sequence analysis of cDNA for a neuronal cell membrane antigen, HPC-1. J. Biol. Chem. 267, 10613–10619.

Irani, M. H. and Kilgore, T. L. 1988. High level expression in yeast. European patent application EP 0 284 044 A1.

Ito, H., Fukuda, Y., Murata, K. and Kimura, A. 1983. Transformation of intact yeast cells with alkali cations. J. Bacteriol. 153, 163–168.

Jeenes, D., MacKenzie, D., Roberts, I. and Archer, D. 1991. Heterologous protein production by filamentous fungi. Biotechnology and Genetic Engineering Reviews, vol. 9. Pp. 327–367.

Keränen, S. 1986. Synthesis and processing of Semliki forest virus polyprotein in *Saccharomyces cerevisiae*: a yeast type glycosylation of E1 envelope protein. Gene 48, 267–275.

Lamsa, M. and Bloebaum, P. 1990. Mutation and screening to increase chymosin yield in a genetically-engineered strain of *Aspergillus avamori*. J. Ind. Microbiol. 5, 229–238.

Lopez, M. C., Nicand, J. M. and Gaillardin, C., 1992. SEC14 deleted mutant of *Yarrowia lipolytica* is altered in the secretion and differentation processes. 16th International Conference on Yeast Genetics and Molecular Biology. Vienna, Austria, Aug. 15–21, 1992, Yeast 8 (Spec. Issue) p. 473.

Maniatis, T., Fritsch, E. F. and Sambrook, J. 1982. Molecular Cloning, A laboratory manual. Cold Spring Harbor Laboratory. Cold Spring Harbor, N.Y.

Martegani, E., Forlani, N., Mauri, I., Porro, D., Schleuning, W. D. and Alberghina, L. 1992. Expression of high levels of human tissue plasminogen activator in yeast under the control of an inducible GAL promoter. Appl. Microbiol. Biotechnol. 37, 604–608.

McKnight, G. L. and McConnaughy, B. L. 1983. Selection of functional cDNAs by complementation in yeast. Proc. Natl. Acad. Sci. USA 80, 4412–4416.

Mäntylä, A., Rossi, H., Vanhanen, S., Penttilä, M., Suominen, P. and Nevalainen, H. 1992. Electrophoretic karyotyping of wild type and mutant *Trichoderma reesei* strains. Current Genetics 21:471–477.

Novick, P. and Scheckman, R., 1979. Secretion and cell-surface growth are blocked in a temperature-sensitive mutant of *Saccharomyces cerevisiae*. Proc. Natl. Acad. Sci. USA 76, 1858–1862.

Novick, P., Ferro, S. and Scheckman, R. 1981. Order of events in the yeast secretory pathway. Cell 25, 461–469.

Novick, P., Fields, C. and Scheckman, R. 1980. Identification of 23 complementation groups required for post-translational events in the yeast secretory pathway. Cell 21, 205–215.

Nyyssönen, E., Keränen, S., Penttilä, M., Takkinen, K. and Knowles, J. K. C. 1990. Immunoglobulin production by Trichoderma. U.S. patent application Ser. No. 552757.

Nyyssönen, E., Penttilä, M., Harkki, A., Saloheimo, A., Knowles, J. K. C. and Keränen, S. 1993. Efficient production of antibodies by the filamentous fungus *Trichoderma reesei*. Bio/Technology 11, 591–595.

Penttilä, M. E., Nevalainen, H., Ratto, M., Salminen, E. and Knowles, J. K. C. 1987. A versatile transformation system for the filamentous fungus *Trichoderma reesei*. Gene 61, 155–164.

Protopopov, V., Govindan, B., Novick, P. and Gerst, J. E. 1993. Homologs of the synaptobrevin/VAMP family of synaptic vesicle proteins function on the late secretory pathway in *S. cerevisiae*. Cell 74, (in press).

Romanos, M. A., Scorer, C. A. and Clare, J. J. 1992. Foreign gene expression in yeast: a Review. Yeast 8, 423–488.

Ruohonen, L., Hackman, P., Lehtovaara, P., Knowles, J. C. K. and Keränen, S. 1987. Efficient secretion of *Bacillus amyloliquefaciens* α-amylase by its own signal peptide in *Saccharomyces cerevisiae* host cells. Gene 59, 161–170.

Ruohonen, L., Penttilä, M. andKerainen, S. 1991. Optimization of Bacillus α-amylase production by *Saccharomyces cerevisiae*. Yeast 7, 337–346.

Sakai, A. Shimizu, Y. and Hishinuma, F. 1988. Isolation and characterization of mutants which show an oversecretion phenotype in *Saccharomyces cerevisiae*. Genetics 119, 499–506.

Schuster, J. R., Moyer, D. L., Lee, H., Dennis, A., Smith, B. and Merryweather, J. P. 1989. Yeast mutants conferring resistance to toxic effects of cloned human insulin-like growth factor I. Gene 83, 47–55.

Segev, N., Mulholland, J. and Botstein, D., 1988. The yeast GTP-binding YTP1-protein and a mammalian counterpart are associated with the secretion machinery. Cell 52, 915–924.

Sikorski, R. S. and Hieter, P. 1989. A system of shuttle vectors and yeast host strains designed for efficient manipulation of DNA in *Saccharomyces cerevisiae*. Genetics 122, 19–27.

Sleep, D., Belfield, G. P., Ballance, D. J., Steven, J., Jones, S. Evans, L. R., Moir, P. D. and Goodey, A. R. 1991. *Saccharomyces cerevisiae* strains that overexpress heterologous proteins. Bio/Technology 9, 183–187.

Smith, R. A., Duncan, M. J. and Moir, D. T. 1985. Heterologous protein secretion from yeast. Science 229, 1219–1224.

Suzuki, K., Ichikawa, K. and Jigami, Y. 1989. Yeast mutants with enhanced ability to secrete human lysozyme: Isolation and identification of a protease-deficient mutant. Mol. Gen. Genet. 219, 58–64.

Vanoni, M., Porro, D., Martegani, E. and Alberghina, L. 1989. Secretion of *Escherichia coli* β-galactosidase in *Saccharomyces cerevisiae* using the signal sequence from the glucoamylase-encoding STA2 gene. Biochem. Biophys. Res. Commun. 164, 1331–1338.

Ward, M., Wilson, L. J., Kodama, K. H., Rey, M. W. and Berka, R. M. 1990. Improved production of calf chymosin in Aspergillus by expression as a glucoamylase-chymosin fusion. Bio/Technology 8, 435–440.

Wilson, D. W., Wilcox, C. A., Flynn, G. C., Chen, E., Unang, W-J., Henzel, W. J., Block, M. R., Ullrich, A. and Rothman, J. E., 1989. A fusion protein required for vehicle-mediated transport in both mammalian cells and yeasts. Nature 339, 355–359.

Zagursky, R. J., Berman, M. L., Baumeister, K. and Lomax, N. 1986. Rapid and easy sequencing of large linear double stranded DNA and supercoiled plasmid DNA. Gene Anal. Techn. 2, 89–94.

Zaraoui, A., Touchot, N., Chardin, P. and Tavitian, A. 1989. The human Rab genes encode family or GTP-binding proteins related to yeast YTP1 and SEC4 products involved in secretion. J. Biol. Chem. 264, 12394–12401.

---

We claim:

1. An isolated DNA sequence of a sec1 suppressor gene SSO selected from the group consisting of SSO1 DNA sequence encoding a polypeptide comprising an amino acid sequence as depicted in SEQ ID NO:2, and SSO2 DNA sequence encoding a polypeptide comprising an amino acid sequence as depicted in SEQ ID NO:4, and fungal homologs of SSO1 and SSO2.

2. A vector comprising a DNA sequence according to claim 1.

3. The vector according to claim 2, wherein said vector is a filamentous fungus expression vector.

4. The vector according to claim 3, wherein expression of DNA in said vector is under control of a regulatory region selected from the group consisting of the sso promoter, the cbh1 promoter, the cbh2 promoter, the egl1 promoter, the egl2 promoter, the tef1 promoter, the pgk promoter, the gpd promoter, the pki promoter, the glucoamylase promoter, the α-amylase promoter, and the alcohol dehydrogenase promoter.

5. The vector according to claim 2, wherein said vector autonomously replicates in a fungal cell.

6. The vector according to claim 2, wherein said vector integrates into the chromosome of a fungal cell.

7. The vector according to claim 2, wherein said vector is a yeast expression vector and wherein gene expression is controlled by yeast regulatory sequences.

8. The vector according to claim 7, wherein said yeast regulatory sequences are selected from the group consisting of the promoter sequence of SSO1, the promoter sequence of SSO2, the promoter sequence of SEC1, the promoter sequence of GAL1, the promoter sequence of GAL10, the promoter sequence of ADH1, and the promoter sequence of an asparagine synthetase gene.

9. The vector according to claim 2, wherein said vector is a fungal vector selected from the group consisting of YEpSSO1 and YEpSSO2.

10. A recombinant fungal host cell comprising a DNA sequence according to claim 1.

11. The recombinant fungal host cell according to claim 10 selected from the group consisting of Saccharomyces spp., Trichoderma spp., Kluyveromyces spp., Schizosaccharomyces pombe, Pichia spp., Hansenula spp., Yarrowia spp., Aspergillus spp., and Neurospora spp.

12. The recombinant fungal host cell according to claim 10 selected from the group consisting of Saccharomyces cerevisiae, strain VTT-C-992072 (DSM 7253) and Saccharomyces cerevisiae, strain VTT-C-92073 (DSM 7254).

13. A method for enhancing expression of Sso protein in a recombinant fungal host cell, comprising the steps of:
   (a) isolating DNA encoding an Sso protein from a suitable donor organism, wherein the Sso protein is selected from the group consisting of the polypeptide as depicted in SEQ ID NO:2, the polypeptide as depicted in SEQ ID NO:4, and polypeptides homologous thereto,
   (b) obtaining a vector comprising said DNA, and
   (c) transforming said vector into a suitable fungal host cell wherein Sso protein expression is enhanced.

14. The method according to claim 13, wherein said suitable fungal host cell is selected from the group consisting Saccharomyces spp., Trichoderma spp., Kluyveromyces spp, Schizosaccharomyces pombe, Pichia spp., Hansenula spp., Yarrowia spp., Aspergillus spp., and Neurospora spp.

15. A method for increasing production of a secreted protein in a fungal host cell, comprising the steps of:
   (a) obtaining a vector comprising an isolated DNA encoding said secreted protein,
   (b) transforming said vector into a suitable fungal host cell having enhanced expression of an SSO gene,
   (c) culturing said host cell under conditions suitable for expression of said secreted protein, and
   (d) purifying said secreted protein from said culture medium.

16. A method for increasing production of a secreted protein in a fungal host cell, comprising the steps of:
   (a) obtaining a vector comprising an isolated DNA encoding said secreted protein,

27

(b) transforming said vector into a suitable fungal host cell having enhanced expression of an SSO gene and a second gene involved in the secretory pathway said second gene being capable of interacting with said SSO gene, (c) culturing said host cell in a suitable culture medium, and (d) purifying said secreted protein from said culture medium.

17. The method according to claim 16, wherein the gene involved in the secretory pathway and interacting with said SSO gene is SEC1 gene.

18. A method for increasing production of an endogenous secreted protein in a fungal host cell, comprising the steps of:

(a) incorporating an SSO DNA sequence selected from the group consisting of SSO1 DNA sequence encoding a polypeptide comprising an amino acid sequence as depicted in SEQ ID NO:2, SSO2 DNA sequence encoding a polypeptide comprising an amino acid sequence as depicted in SEQ ID NO:4, and homologs thereof, into a fungal host cell which produces said endogenous secreted protein, (b) screening for host cells in which expression of endogenous secreted protein is enhanced, (c) culturing said host cells in a suitable culture medium, and (d) purifying said endogenous secreted protein from said culture medium.

19. A method of biomass production in a fungal host cell, comprising the steps of:

(a) obtaining a fungal vector comprising an isolated DNA encoding a hydrolytic enzyme, (b) transforming said fungal vector into a suitable fungal host cell expressing enhanced levels of SSO genes, and (c) culturing said host cells in a culture medium suitable for biomass production.

28

20. A method for biomass production in a fungal host cell, comprising the steps of:

(a) obtaining a fungal vector comprising an isolated DNA encoding a hydrolytic enzyme, (b) transforming said fungal vector into a suitable fungal host cell expressing enhanced levels of SSO genes, and genes involved in the secretory pathway being capable of interacting with said SSO genes, (c) culturing said host cells in a culture medium suitable for biomass production.

21. The method according to claim 20, wherein the gene involved in the secretory pathway is capable of interacting with said SSO gene is SEC1 gene.

22. A method for increasing production of an endogenous secreted protein in a fungal a host cell, comprising the steps of:

(a) incorporating an SSO gene selected from the group consisting of SSO1 DNA sequence encoding a polypeptide comprising an amino acid sequence as depicted in SEQ ID NO:2, and SSO2 DNA sequence encoding a polypeptide comprising an amino acid sequence as depicted in SEQ ID NO:4, and homologs thereof, and a second gene involved in the secretory pathway said second gene being capable of interacting with said SSO gene, into a fungal host cell which produces said endogenous secreted protein, (b) selecting host cells in which expression of endogenous secreted protein is enhanced, (c) culturing said host cells in a suitable culture medium, and (d) isolating said endogenous secreted protein from said culture medium.

23. The method according to claim 22, wherein the second gene involved in the secretory pathway is capable of interacting with said SSO gene is SEC1 gene.

* * * * *